US012114841B2

(12) United States Patent
Nock et al.

(10) Patent No.: US 12,114,841 B2
(45) Date of Patent: *Oct. 15, 2024

(54) APPARATUS TO ALLOW BIOPSY SAMPLE VISUALIZATION DURING TISSUE REMOVAL

(71) Applicant: Devicor Medical Products, Inc., Cincinnati, OH (US)

(72) Inventors: Andrew Paul Nock, Dayton, OH (US); Jessica P. Leimbach, Cincinnati, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 740 days.

This patent is subject to a terminal disclaimer.

(21) Appl. No.: 17/016,550

(22) Filed: Sep. 10, 2020

(65) Prior Publication Data

US 2020/0405276 A1 Dec. 31, 2020

Related U.S. Application Data

(63) Continuation of application No. 16/117,398, filed on Aug. 30, 2018, now Pat. No. 10,799,222, which is a
(Continued)

(51) Int. Cl.
*A61B 10/02* (2006.01)
*A61B 10/00* (2006.01)
*A61B 90/00* (2016.01)

(52) U.S. Cl.
CPC ...... *A61B 10/0275* (2013.01); *A61B 10/0096* (2013.01); *A61B 10/0283* (2013.01);
(Continued)

(58) Field of Classification Search
None
See application file for complete search history.

(56) References Cited

U.S. PATENT DOCUMENTS 3,659,587 A * 5/1972 Baldwin .......... A61B 5/150503
600/577
5,271,414 A * 12/1993 Partika ............... A61B 10/0266
600/567
(Continued)

FOREIGN PATENT DOCUMENTS

| EP | 2062537 A1 | 5/2009 |
| WO | WO 2007/021904 A2 | 2/2007 |
| WO | WO 2017/075415 A1 | 5/2017 |

OTHER PUBLICATIONS

International Search Report and Written Opinion for International Application No. PCT/US2017/064261, dated Apr. 9, 2018, 16 pages.

*Primary Examiner* — Matthew Kremer
(74) *Attorney, Agent, or Firm* — Frost Brown Todd LLP

(57) ABSTRACT

A biopsy device includes a body, a needle, a cutter, a tissue sample holder, and a gate assembly. The needle extends distally from the body. The cutter is longitudinally translatable relative to the needle and defines a cutter lumen. The tissue sample holder is coupled proximally relative to the body. The cutter lumen of the cutter defines at least a portion of a fluid conduit extending between the cutter and the tissue sample holder. The gate assembly is configured to selectively arrest movement of a tissue sample holder within the fluid conduit between the cutter and the tissue sample holder.

20 Claims, 20 Drawing Sheets

Related U.S. Application Data continuation of application No. 15/829,483, filed on Dec. 1, 2017, now abandoned.

(60) Provisional application No. 62/429,379, filed on Dec. 2, 2016.

(52) U.S. Cl.
CPC . *A61B 2010/009* (2013.01); *A61B 2010/0208* (2013.01); *A61B 2010/0225* (2013.01); *A61B 2090/036* (2016.02)

(56) References Cited

U.S. PATENT DOCUMENTS

| | | | |
|---|---|---|---|
| 5,526,822 A | 6/1996 | Burbank et al. | |
| 5,928,164 A | 7/1999 | Burbank et al. | |
| 6,017,316 A | 1/2000 | Ritchart et al. | |
| 6,086,544 A | 7/2000 | Hibner et al. | |
| 6,162,187 A | 12/2000 | Buzzard et al. | |
| 6,432,065 B1 | 8/2002 | Burdorff et al. | |
| 6,547,432 B2 | 4/2003 | Coffeen et al. | |
| 6,626,849 B2 | 9/2003 | Huitema et al. | |
| 6,752,768 B2 | 6/2004 | Burdorff et al. | |
| 7,442,171 B2 | 10/2008 | Stephens et al. | |
| 7,648,466 B2 | 1/2010 | Stephens et al. | |
| 7,837,632 B2 | 11/2010 | Stephens et al. | |
| 7,854,706 B2 | 12/2010 | Hibner | |
| 7,914,464 B2 | 3/2011 | Burdorff et al. | |
| 7,938,786 B2 | 5/2011 | Ritchie et al. | |
| 8,083,687 B2 | 12/2011 | Parihar | |
| 8,105,243 B2 | 1/2012 | Vetter | |
| 8,118,755 B2 | 2/2012 | Hibner et al. | |
| 8,206,316 B2 | 6/2012 | Hibner et al. | |
| 8,241,226 B2 | 8/2012 | Hibner et al. | |
| 8,337,415 B2 | 12/2012 | Trezza, II et al. | |
| 8,454,531 B2 | 6/2013 | Speeg et al. | |
| 8,486,155 B2 | 7/2013 | McAlister et al. | |
| 8,535,268 B2 | 9/2013 | Auld et al. | |
| 8,622,924 B2 | 1/2014 | Speeg et al. | |
| 8,702,623 B2 | 4/2014 | Parihar et al. | |
| 8,764,680 B2 | 6/2014 | Rhad et al. | |
| 8,801,742 B2 | 8/2014 | Rhad et al. | |
| 8,858,465 B2 | 10/2014 | Fiebig | |
| 8,938,285 B2 | 1/2015 | Fiebig et al. | |
| 8,992,487 B2 | 3/2015 | Eich et al. | |
| 9,095,326 B2 | 8/2015 | Ritchie et al. | |
| 9,138,543 B2 | 9/2015 | Frantz et al. | |
| 9,326,755 B2 | 5/2016 | Fiebig et al. | |
| 9,345,457 B2 | 5/2016 | Speeg et al. | |
| 9,486,186 B2 | 11/2016 | Fiebig et al. | |
| 9,492,130 B2 | 11/2016 | Flagle et al. | |
| 9,999,751 B2 | 6/2018 | Pacheco et al. | |
| 10,010,359 B2 | 7/2018 | Garcia et al. | |
| 10,064,607 B2 | 9/2018 | Keller et al. | |
| 10,201,331 B2 | 2/2019 | Fleming et al. | |
| 10,335,122 B2 | 7/2019 | Nock et al. | |
| 10,398,415 B2 | 9/2019 | Nock et al. | |
| 10,799,222 B2 * | 10/2020 | Nock | A61B 10/0275 |
| 11,241,222 B2 * | 2/2022 | Nock | A61B 10/0283 |
| 2006/0074345 A1 | 4/2006 | Hibner | |
| 2007/0239067 A1 | 10/2007 | Hibner et al. | |
| 2008/0119881 A1 * | 5/2008 | Vetter | A61B 10/0041 606/170 |
| 2008/0140092 A1 * | 6/2008 | Stone | A61B 17/04 606/139 |
| 2008/0188833 A1 * | 8/2008 | Taufig | A61M 1/84 604/540 |
| 2009/0131821 A1 | 5/2009 | Speeg et al. | |
| 2010/0152610 A1 | 6/2010 | Parihar et al. | |
| 2010/0160819 A1 | 6/2010 | Parihar et al. | |
| 2011/0208087 A1 * | 8/2011 | Trezza, II | A61B 17/320016 600/567 |
| 2011/0282324 A1 | 11/2011 | Kurokawa et al. | |
| 2011/0282382 A1 * | 11/2011 | McAlister | A61M 5/19 606/213 |
| 2013/0144188 A1 | 6/2013 | Fiebig et al. | |
| 2013/0218047 A1 | 8/2013 | Fiebig et al. | |
| 2013/0231585 A1 * | 9/2013 | Flagle | G01N 35/04 600/565 |
| 2013/0324882 A1 | 12/2013 | Mescher et al. | |
| 2015/0065913 A1 * | 3/2015 | Keller | A61B 10/0266 600/566 |
| 2018/0153526 A1 | 6/2018 | Nock et al. | |
| 2018/0153529 A1 | 6/2018 | Nock et al. | |

* cited by examiner

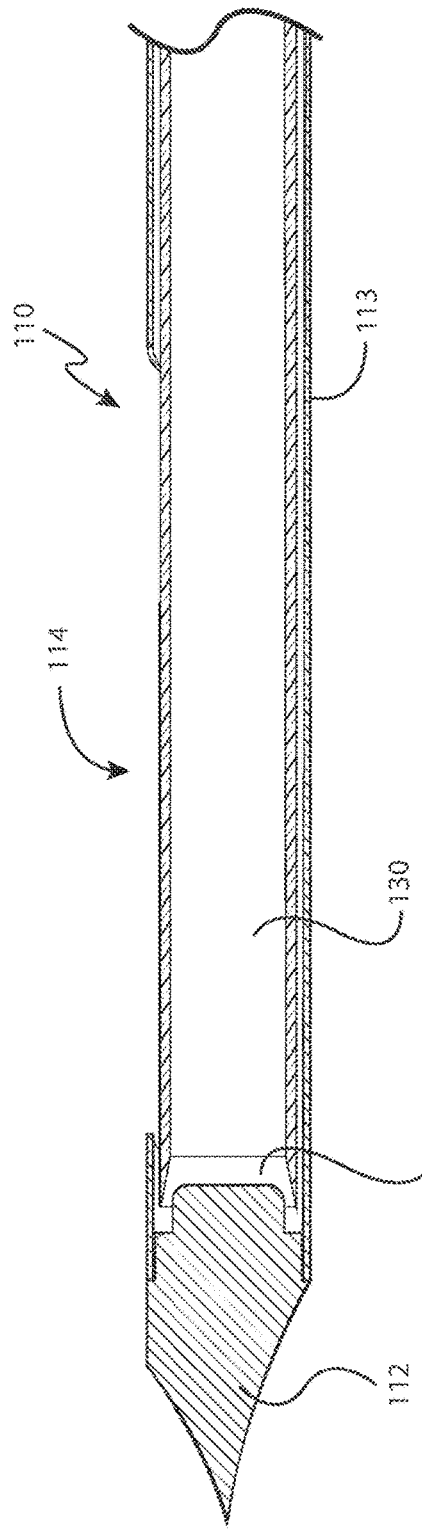
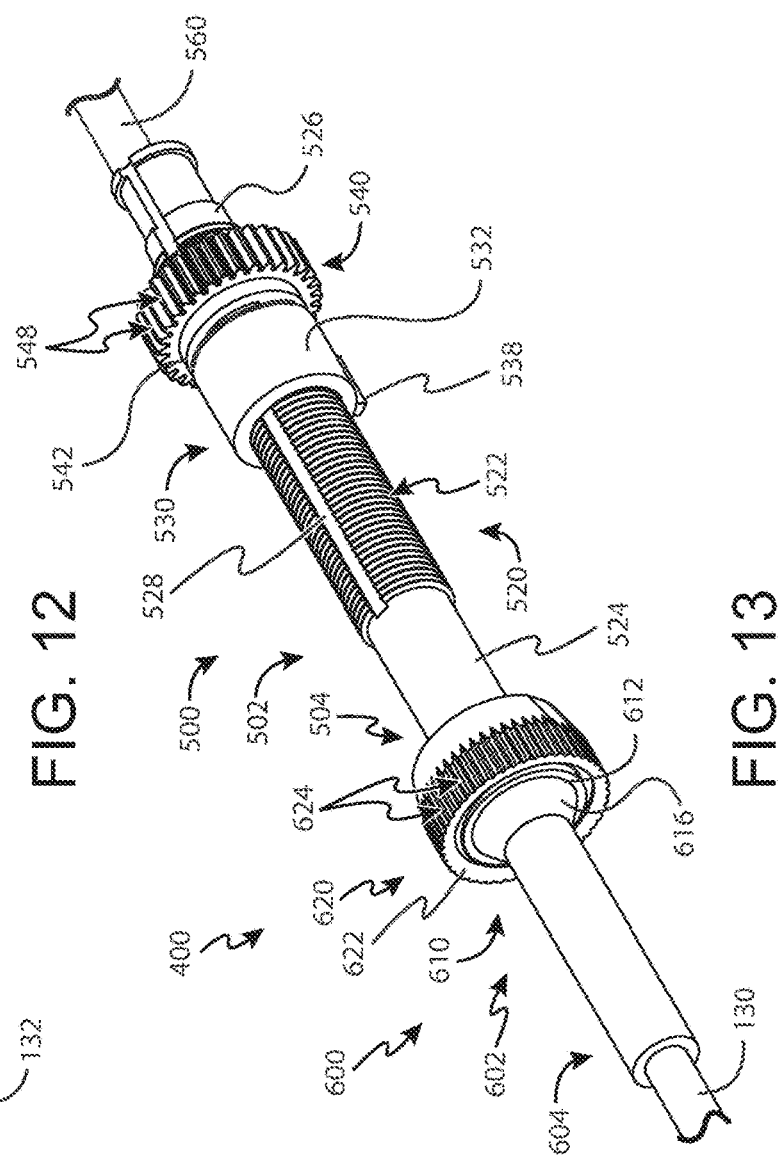
FIG. 12
FIG. 13

APPARATUS TO ALLOW BIOPSY SAMPLE VISUALIZATION DURING TISSUE REMOVAL

PRIORITY

This present application is a continuation of U.S. Ser. No. 16/117,398, entitled "Apparatus to Allow Biopsy Sample Visualization During Tissue Removal," filed Aug. 30, 2018, which is a continuation of U.S. Ser. No. 15/829,483, entitled "Apparatus to Allow Biopsy Sample Visualization During Tissue Removal," filed Dec. 1, 2017, which claims priority to U.S. Provisional Patent Application No. 62/429,379, entitled "Apparatus to Allow Biopsy Sample Visualization During Tissue Removal," filed Dec. 2, 2016 the disclosures of which are hereby incorporated by reference herein in entirety.

BACKGROUND

A biopsy is the removal of a tissue sample from a patient to enable examination of the tissue for signs of cancer or other disorders. Tissue samples may be obtained in a variety of ways using various medical procedures involving a variety of the sample collection devices. For example, biopsies may be open procedures (surgically removing tissue after creating an incision) or percutaneous procedures (e.g. by fine needle aspiration, core needle biopsy, or vacuum assisted biopsy). After the tissue sample is collected, the tissue sample may be analyzed at a lab (e.g. a pathology lab, biomedical lab, etc.) that is set up to perform the appropriate tests (such as histological).

Merely exemplary biopsy devices and biopsy system components are disclosed in U.S. Pat. No. 5,526,822, entitled "Method and Apparatus for Automated Biopsy and Collection of Soft Tissue," issued Jun. 18, 1996; U.S. Pat. No. 5,928,164, entitled "Apparatus for Automated Biopsy and Collection of Soft Tissue," issued Jul. 27, 1999; U.S. Pat. No. 6,086,544, entitled "Control Apparatus for an Automated Surgical Biopsy Device," issued Jul. 11, 2000; U.S. Pat. No. 6,162,187, entitled "Fluid Collection Apparatus for a Surgical Device," issued Dec. 19, 2000; U.S. Pat. No. 6,432,065, entitled "Method for Using a Surgical Biopsy System with Remote Control for Selecting an Operational Mode," issued Aug. 13, 2002; U.S. Pat. No. 6,752,768, entitled "Surgical Biopsy System with Remote Control for Selecting an Operational Mode," issued Jun. 22, 2004; U.S. Pat. No. 7,442,171, entitled "Remote Thumbwheel for a Surgical Biopsy Device," issued Oct. 8, 2008; U.S. Pat. No. 7,854,706, entitled "Clutch and Valving System for Tetherless Biopsy Device," issued Dec. 1, 2010; U.S. Pat. No. 7,914,464, entitled "Surgical Biopsy System with Remote Control for Selecting an Operational Mode," issued Mar. 29, 2011; U.S. Pat. No. 7,938,786, entitled "Vacuum Timing Algorithm for Biopsy Device," issued May 10, 2011; U.S. Pat. No. 8,118,755, entitled "Biopsy Sample Storage," issued Feb. 21, 2012; U.S. Pat. No. 8,206,316, entitled "Tetherless Biopsy Device with Reusable Portion," issued Jun. 26, 2012; U.S. Pat. No. 8,241,226, entitled "Biopsy Device with Rotatable Tissue Sample Holder," issued Aug. 14, 2012; U.S. Pat. No. 8,764,680, entitled "Handheld Biopsy Device with Needle Firing," issued Jul. 1, 2014; U.S. Pat. No. 8,801,742, entitled "Needle Assembly and Blade Assembly for Biopsy Device," issued Aug. 12, 2014; U.S. Pat. No. 8,938,285, entitled "Access Chamber and Markers for Biopsy Device," issued Jan. 20, 2015; U.S. Pat. No. 8,858,465, entitled "Biopsy Device with Motorized Needle Firing," issued Oct. 14, 2014; U.S. Pat. No. 9,326,755, entitled "Biopsy Device Tissue Sample Holder with Bulk Chamber and Pathology Chamber," issued May 3, 2016; and U.S. Pat. No. 9,345,457, entitled "Presentation of Biopsy Sample by Biopsy Device," issued May 24, 2016. The disclosure of each of the above-cited U.S. patents is incorporated by reference herein.

Additional exemplary biopsy devices and biopsy system components are disclosed in U.S. Pat. Pub. No. 2006/0074345, entitled "Biopsy Apparatus and Method," published Apr. 6, 2006, now abandoned; U.S. Pat. Pub. No. 2009/0131821, entitled "Graphical User Interface For Biopsy System Control Module," published May 21, 2009, now abandoned; U.S. Pat. Pub. No. 2010/0160819, entitled "Biopsy Device with Central Thumbwheel," published Jun. 24, 2010; and U.S. Pat. Pub. No. 2013/0324882, entitled "Control for Biopsy Device," published Dec. 5, 2013, now abandoned. The disclosure of each of the above-cited U.S. patent application Publications, U.S. Non-Provisional patent Applications, and U.S. Provisional patent applications is incorporated by reference herein.

While several systems and methods have been made and used for obtaining and processing a biopsy sample, it is believed that no one prior to the inventor has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 12 depicts another side cross-sectional view of the needle of FIG. 3, the cross-section taken along line 4-4 of FIG. 2, with the cutter in a distal position and a lateral aperture in a closed configuration;

FIG. 13 depicts another perspective view of the sample acquisition assembly of FIG. 2, with the cutter actuation assembly in a distal position and the gate assembly in the closed position;

Figure 1:
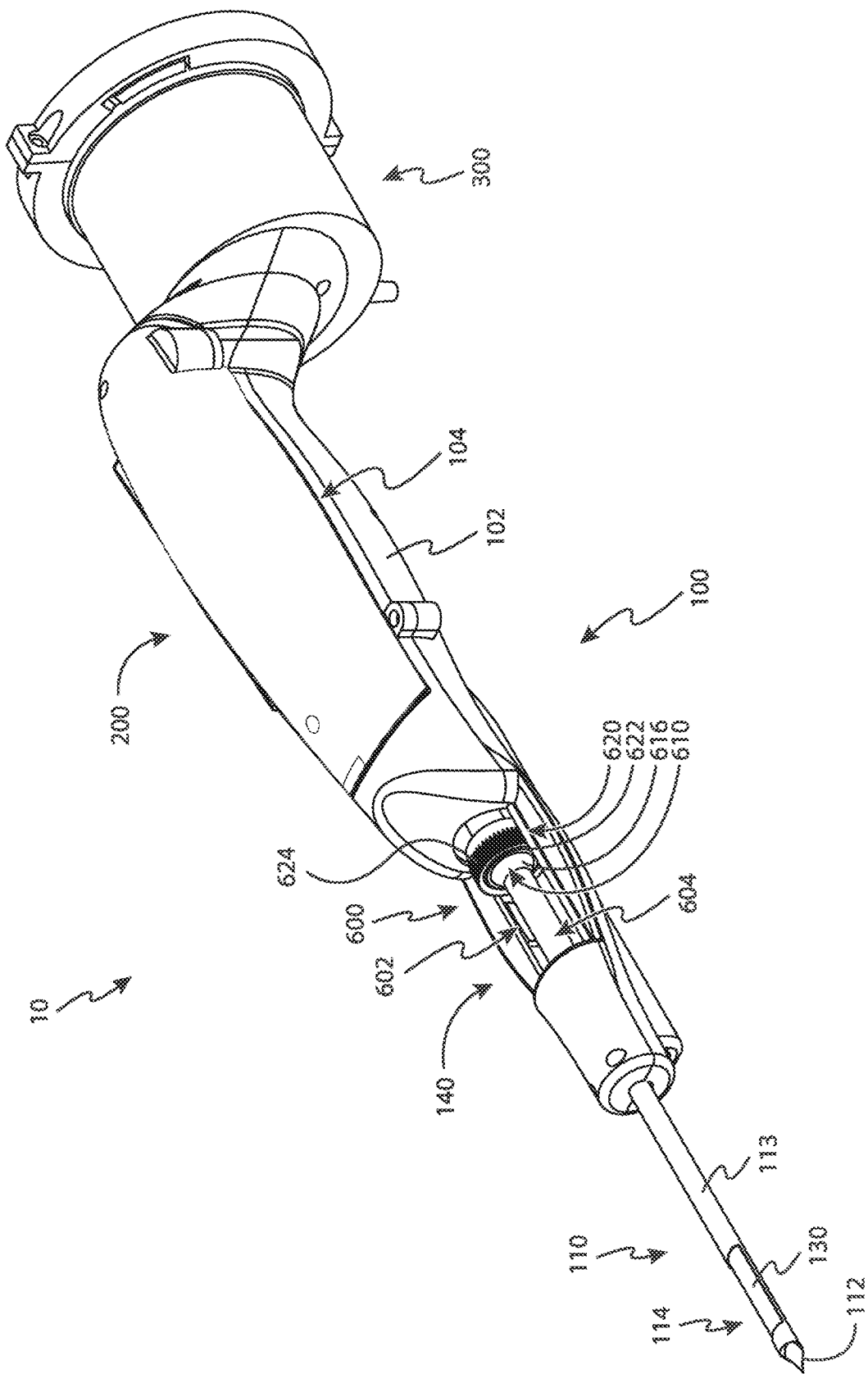
FIG. 1 depicts perspective view of an exemplary biopsy device.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. EXEMPLARY BIOPSY DEVICE

FIG. 1 shows an exemplary a biopsy device (10) that may be used in a breast biopsy system including, in some examples, a vacuum control module (not shown). Biopsy device (10) of the present example comprises a probe (100) and a holster (200). A needle (110) extends distally from probe (100), and is inserted into a patient's tissue to obtain tissue samples. These tissue samples are deposited in a tissue sample holder (300) at the proximal end of probe (100), as will also be described in greater detail below.

Holster (200) of the present example is selectively attachable to probe (100) to provide actuation of various components within probe (100). In the present configuration, holster (200) is a reusable component, while probe (100) and tissue sample holder (300) are disposable. It should be understood that the use of the term "holster" herein should not be read as requiring any portion of probe (100) to be inserted into any portion of holster (200). For instance, in the present example, holster (200) includes a set of prongs (not shown) or other retention features that are received by probe (100) to releasably secure probe (100) to holster (200). Probe (100) also includes a set of resilient tabs (not shown) or other suitable release features that may be pressed inwardly to disengage the prongs, such that a user may simultaneously depress both of the tabs then pull probe (100) rearwardly and away from holster (200) to decouple probe (100) from holster (200). Of course, a variety of other types of structures, components, features, etc. (e.g., bayonet mounts, latches, clamps, clips, snap fittings, etc.) may be used to provide removable coupling of probe (100) and holster (200). Furthermore, in some biopsy devices (10), probe (100) and holster (200) may be of unitary or integral construction, such that the two components cannot be separated. By way of example only, in versions where probe (100) and holster (200) are provided as separable components, probe (100) may be provided as a disposable component, while holster (200) may be provided as a reusable component. Still other suitable structural and functional relationships between probe (100) and holster (200) will be apparent to those of ordinary skill in the art in view of the teachings herein.

Some variations of biopsy device (10) may include one or more sensors (not shown), in probe (100) and/or in holster (200), that is/are configured to detect when probe (100) is coupled with holster (200). Such sensors or other features may further be configured to permit only certain types of probes (100) and holsters (200) to be coupled together. In addition, or in the alternative, such sensors may be configured to disable one or more functions of probes (100) and/or holsters (200) until a suitable probe (100) and holster (200) are coupled together. In one merely illustrative example, probe (100) includes a magnet (not shown) that is detected by a Hall Effect sensor (not shown) or some other type of sensor in holster (200) when probe (100) is coupled with holster (200). As yet another merely illustrative example, coupling of probe (100) with holster (200) may be detected using physical contact between conductive surfaces or electrodes, using RFID technology, and/or in numerous other ways as will be apparent to those of ordinary skill in the art in view of the teachings herein. Of course, such sensors and features may be varied or omitted as desired.

Biopsy device (10) of the present example is configured for handheld use, and be used under ultrasonic guidance. Of course, biopsy device (10) may instead be used under stereotactic guidance, MRI guidance, PEM guidance, BSGI guidance, or otherwise. It should also be understood that biopsy device (10) may be sized and configured such that biopsy device (10) may be operated by a single hand of a user. In particular, a user may grasp biopsy device (10), insert needle (110) into a patient's breast, and collect one or a plurality of tissue samples from within the patient's breast, all with just using a single hand. Alternatively, a user may grasp biopsy device (10) with more than one hand and/or with any desired assistance. In still other examples, biopsy device (10) can be configured to be secured to a table or other fixture without handheld operation.

In some settings, whether biopsy device (10) is handheld or mounted to a fixture, the user may capture a plurality of tissue samples with just a single insertion of needle (110) into the patient's breast. Such tissue samples may be deposited in tissue sample holder (300), and later retrieved from tissue sample holder (300) for analysis. While examples described herein often refer to the acquisition of biopsy samples from a patient's breast, it should be understood that biopsy device (10) may be used in a variety of other procedures for a variety of other purposes and in a variety of other parts of a patient's anatomy (e.g., prostate, thyroid, etc.). Various exemplary components, features, configurations, and operabilities of biopsy device (10) will be described in greater detail below; while other suitable components, features, configurations, and operabilities will be apparent to those of ordinary skill in the art in view of the teachings herein.

Holster (200) of the present example includes an outer housing (210) that is configured to at least partially encompass the internal components of holster (200). Although not shown, it should be understood that holster (200) of the present example includes one or more motors and/or other actuators that are configured to drive various components of probe. To communicate power or movement to probe (100), holster (200) can include one or more gears. For instance, in some examples, one or more gears at least partially extend through an opening in outer housing (210). The opening in outer housing (210) can be configured to align with a corresponding opening associated with probe (100) to thereby permit the one or more gears of holster (200) to mesh with one or more corresponding gears of probe (100).

Although not shown, it should be understood that holster (200) may also include various cables that are configured to couple holster (200) to a control module or another control feature. Suitable cables may include electrical cables, rotary drive cables, pneumatic cables, or some combination thereof. Accordingly, it should be understood that in some examples, internal components within holster (200) may be powered by electrical power (electrical cables), rotary power (rotary drive cable), and/or pneumatic power (pneumatic cables). Alternatively, in some examples the cables are omitted entirely and holster (200) can be battery powered with motors and vacuum pumps being entirely contained within holster (200).

As described above, holster (200) of the present example is configured as a reusable portion, while probe (100) is configured as a disposable portion. In some contexts, it may be desirable to maintain sterility of reusable components during a biopsy procedure. Accordingly, in some instances it may be desirable to use holster (200) in connection with certain features to maintain the sterility of holster (200), while also maintaining functionality of holster (200). Merely exemplary features and methods for maintaining the sterility of holster (200) are shown and described in U.S. Pat. App. No. 62/429,356, entitled "Functional Cover for Biopsy Device," filed on Dec. 2, 2016, the disclosure of which is incorporated by reference herein.

Probe (100) of the present example includes a needle (110) extending distally from probe (100) that is inserted into a patient's tissue to obtain tissue samples. These tissue samples are deposited in a tissue sample holder (300) at the proximal end of probe (100). In some examples, a vacuum control module (not shown) is coupled with probe (100) via a valve assembly (not shown) and tubes (not shown), which is operable to selectively provide vacuum, saline, atmospheric air, and venting to probe (100). By way of example only, the internal components of the valve assembly of the present example may be configured and arranged as described in U.S. Pat. Pub. No. 2013/0218047, entitled "Biopsy Device Valve Assembly," published Aug. 22, 2013, the disclosure of which is incorporated by reference herein.

As described above with respect to holster (200), probe (100) is selectively couplable to holster (200) so that holster (200) may provide power or otherwise actuate probe (100). In particular, probe (100) includes an outer housing (102) that includes a holster receiving portion (104) that is configured to receive holster (200). In some examples, holster receiving portion (104) includes an opening that is configured to align with a corresponding opening of holster (200). One or more drive gears (540) are exposed through the opening in outer housing (102), and are operable to drive a cutter actuation mechanism in probe (100). The one or more drive gears (540) of probe (100) mesh with the one or more gears of holster (200) when probe (100) and holster (200) are coupled together. Accordingly, holster (200) may provide mechanical power or otherwise drive movement of components within probe (100) via gears of probe (100) and holster (200).

Outer housing (102) of probe (100) additionally defines a sample window (140) disposed distally on the exterior of outer housing (102) adjacent to the distal end of outer housing (102). In some examples, it may be desirable for an operator to view samples as they are collected by needle (110). For instance, and as will be described in greater detail below, in the present example tissue sample holder (300) is configured to collect tissue sample in a bulk configuration. While this configuration of tissue sample collection may enhance tissue sample capacity, the ability to visualize individual tissue samples may be reduced due to multiple tissue samples being comingled within a common space. Accordingly, sample window (140) is configured to permit an operator to visualize individual tissue samples as they are collected via needle (110). As will be described in greater detail below, sample window (140) permits an operator to visually inspect a severed tissue sample prior to transportation of the severed tissue sample to tissue sample holder (300).

Needle (110) of the present example comprises a cannula (113) having a piercing tip (112), and a lateral aperture (114) located proximal to tip (112). Tissue piercing tip (112) is configured to pierce and penetrate tissue, without requiring a high amount of force, and without requiring an opening to be pre-formed in the tissue prior to insertion of tip (112). Alternatively, tip (112) may be blunt (e.g., rounded, flat, etc.) if desired. By way of example only, tip (112) may be configured in accordance with any of the teachings in U.S. Pat. No. 8,801,742, entitled "Needle Assembly and Blade Assembly for Biopsy Device," filed Jun. 1, 2011, the disclosure of which is incorporated by reference herein. As another merely illustrative example, tip (112) may be configured in accordance with at least some of the teachings in U.S. Pat. Pub. No. 2013/0144188, entitled "Biopsy Device with Slide-In Probe," published Jun. 6, 2013, will issue on Nov. 8, 2016 as U.S. Pat. No. 9,486,186, the disclosure of which is incorporated by reference herein. Other suitable configurations that may be used for tip (112) will be apparent to those of ordinary skill in the art in view of the teachings herein.

Lateral aperture (114) is sized to receive prolapsed tissue during operation of device (10). A hollow tubular cutter (130) having a sharp distal edge (132) is located within needle (110). Cutter (130) is operable to rotate and translate relative to needle (110) and past lateral aperture (114) to sever a tissue sample from tissue protruding through lateral aperture (114). For instance, cutter (130) may be moved from an extended position to a retracted position, thereby "opening" lateral aperture (114) to allow tissue to protrude therethrough; then from the retracted position back to the extended position to sever the protruding tissue.

In some examples it may be desirable to rotate needle (110) to orient lateral aperture (114) at a plurality of desired angular positions about the longitudinal axis of needle (110). In the present example, needle (110) can be rotated by a motor disposed in probe (100) or holster (200). In other examples, needle (110) is manually rotatable by a thumbwheel on probe (100) or needle hub directly overmolded onto needle (110). Regardless, it should also be understood that, as with other components described herein, needle (110) may be varied, modified, substituted, or supplemented in a variety of ways; and that needle (110) may have a variety of alternative features, components, configurations, and functionalities. For instance, needle (110) may be constructed in accordance with the teachings of U.S. Pat. No. 9,345,457, issued May 24, 2016, the disclosure of which is incorporated by reference herein, and/or in accordance with the teachings of any other reference cited herein.

Tissue sample holder (300) is selectively coupleable to the proximal end of probe (100). In the present example, tissue sample holder (300) is configured to receive a plurality of tissue samples in a variety of tissues sample collection configurations. By way of example only, suitable tissue collection configurations may include bulk tissue sample collection configurations and/or individual sample collection configurations. In a bulk sample collection configuration, acquired tissue samples are comingled within one or more tissue sample collection chambers. By contrast, in an individual sample collection configuration, tissue samples are segregated in individual sample compartments. While tissue sample holder (300) in some examples may be configured for exclusively bulk sample collection or individual sample collection, it should be understood that in other examples both tissue sample collection configurations can be combined in a single tissue sample holder (300). Merely exemplary configurations for tissue sample holder shown and described in International Pat. App. No. PCT/US2016/059411, entitled "Tissue Sample Holder with Bulk Tissue Collection Feature," filed on Oct. 28, 2016; and U.S. Pat. App. No. 62/429,471, entitled "Multi-Chamber Tissue Sample Cup for Biopsy Device," filed on Dec. 2, 2016, the disclosures of which are incorporated by reference herein.

II. EXEMPLARY TISSUE ACQUISITION ASSEMBLY

Figure 2:
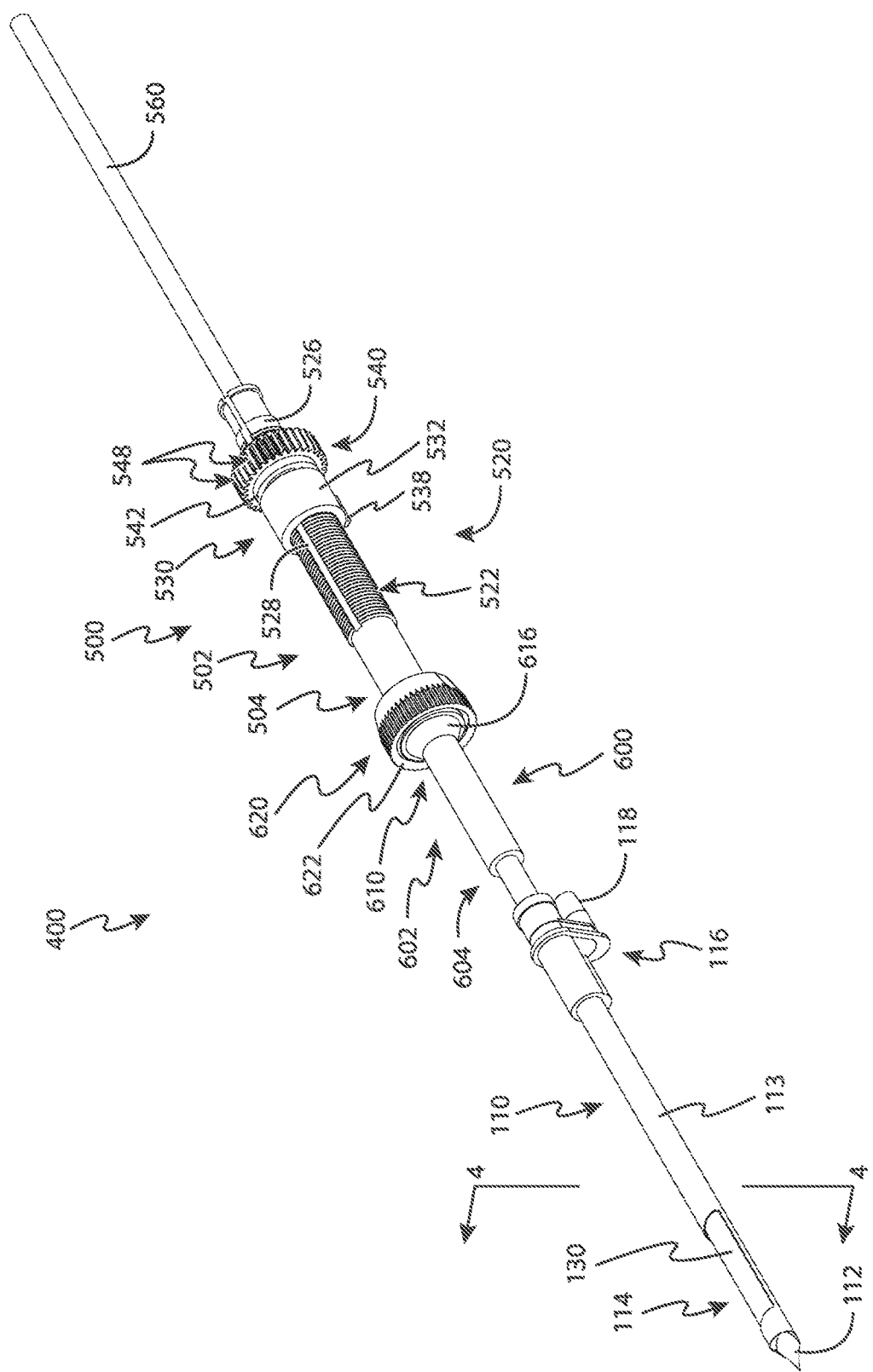
FIG. 2 depicts a perspective of a tissue sample acquisition assembly of the biopsy device of FIG. 1.

As best seen in FIG. 2, probe (100) further includes a tissue acquisition assembly (400). As can be seen, tissue acquisition assembly (400) comprises needle (110), cutter (130), a cutter actuation assembly (500), and a gate assembly (600). As described above, needle (110) comprises a cannula (113) and a tissue piercing tip (112). Cannula (113) of the present example comprises a generally circular cross-sectional shape, defining a lumen therein such that cannula (113) is configured to receive cutter (130) coaxially within the lumen of cannula (113). Tissue piercing tip (112) is secured to the distal end of cannula (113). In the present example, tissue piercing tip (112) is a solid homogeneous piece of material that is ground to form a plurality of facets that together define the sharp point of tissue piercing tip (112). Although tissue piercing tip (112) of the present example is shown as a single part, it should be understood that in other examples tissue piercing tip (112) comprises a multiple part assembly. Merely exemplary alternative configurations for tissue piercing tip (112) are shown and described in U.S. Pat. No. 8,801,742, entitled "Needle Assembly and Blade Assembly for Biopsy Device," issued on Aug. 12, 2014, the disclosure of which is incorporated by reference herein.

Figure 3:
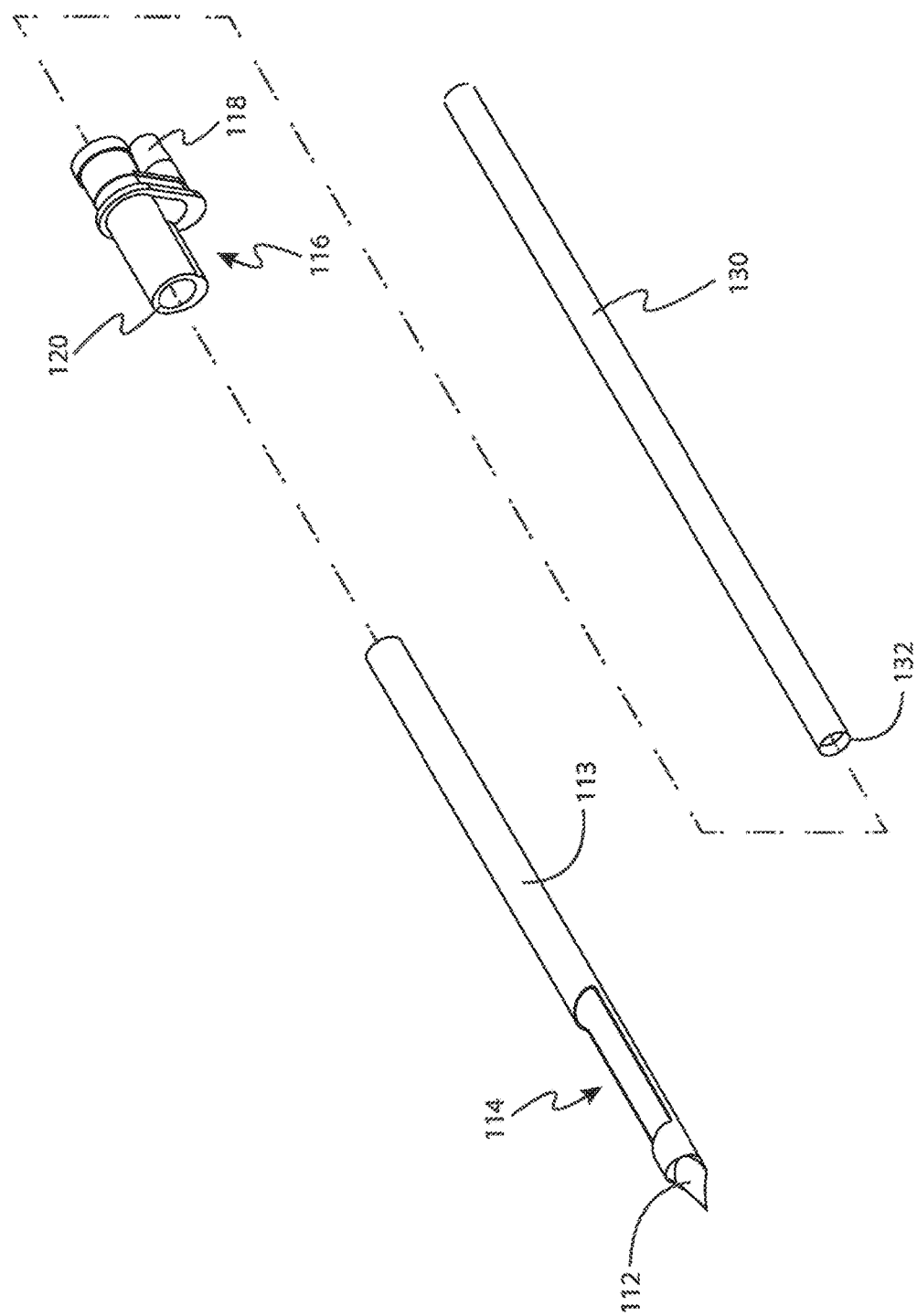
FIG. 3 depicts an exploded perspective view of a needle of the tissue acquisition assembly of FIG. 2.
Figure 4:
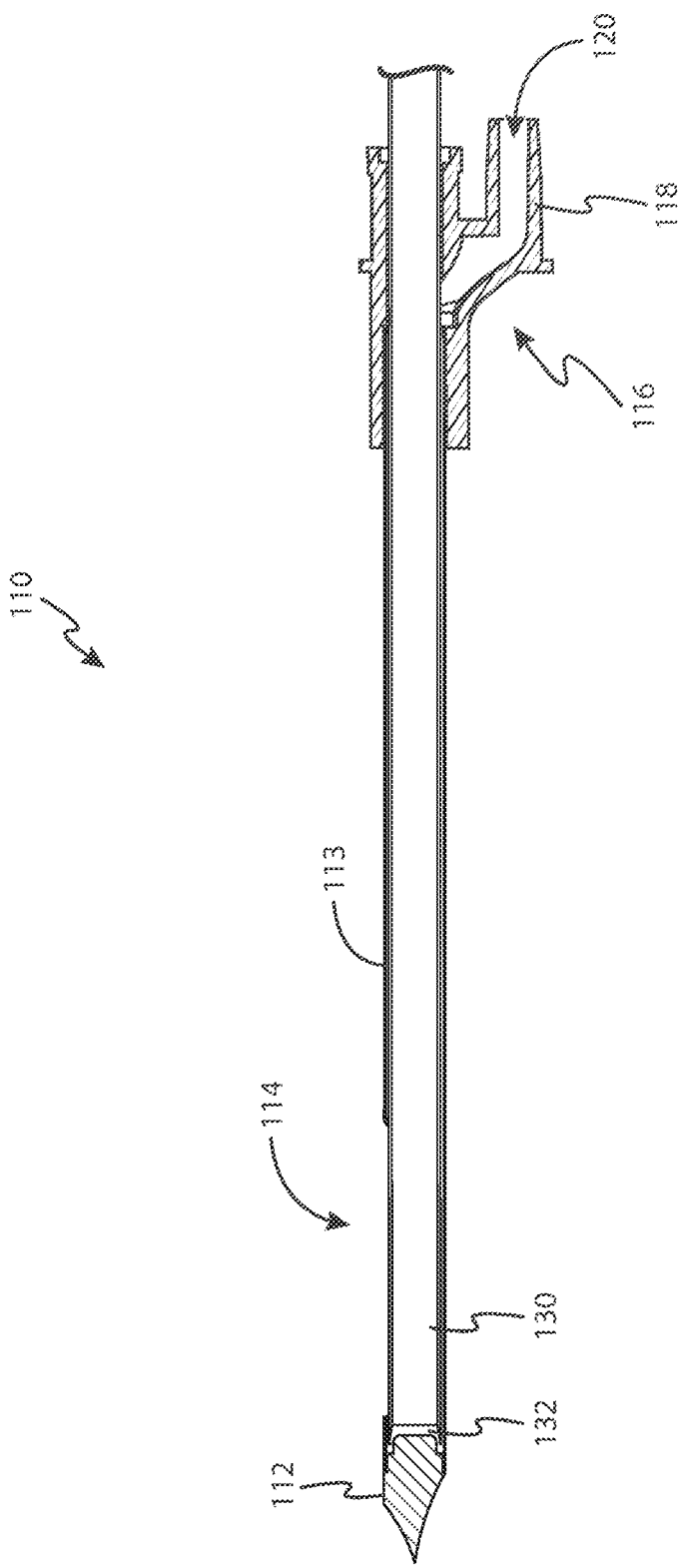
FIG. 4 depicts a side cross-sectional view of the needle of FIG. 3, with the cross-section taken along line 4-4 of FIG. 2.

As can be best seen in FIGS. 3 and 4, needle (110) additionally includes a manifold (116) secured to the distal end of cannula (113). Manifold (116) is generally configured to direct fluid into the lumen of cannula (113). Manifold (116) includes a port (118) and a lumen (120) communicating with port (118). Although not shown, it should be understood that a tube or valve assembly can be connected to port (118) to communicate fluids into lumen (120). Lumen (120) extends through manifold (116) and into communication with the lumen of cutter (130). Accordingly, it should be understood that fluids may be directed to port (118) and into lumen (120) to communicate fluids to the lumen of cannula (113). In use, any suitable fluid may be communicated through manifold (116). For instance, in some examples manifold (116) is used to provide atmospheric air to the lumen of cannula (113). In such examples, atmospheric air may be desirable to enhance transportation of tissue samples through cutter (130) by providing a pressure differential on either side of the tissue sample. In addition, in some examples manifold (116) is used to provide vacuum and/or saline to assist with a biopsy procedure.

Figure 5:
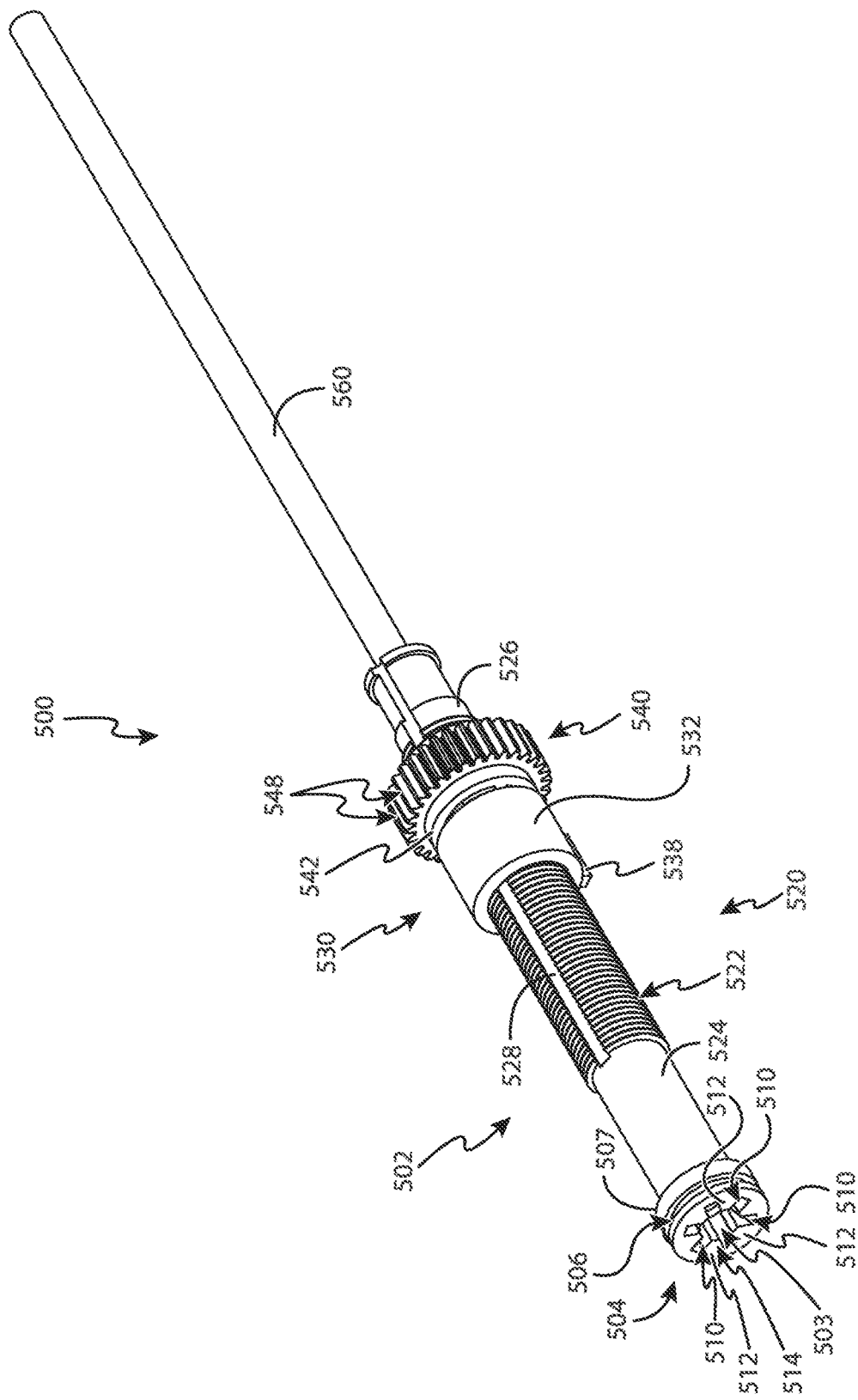
FIG. 5 depicts a perspective view of a cutter actuation assembly of the sample acquisition assembly of FIG. 2.
Figure 6:
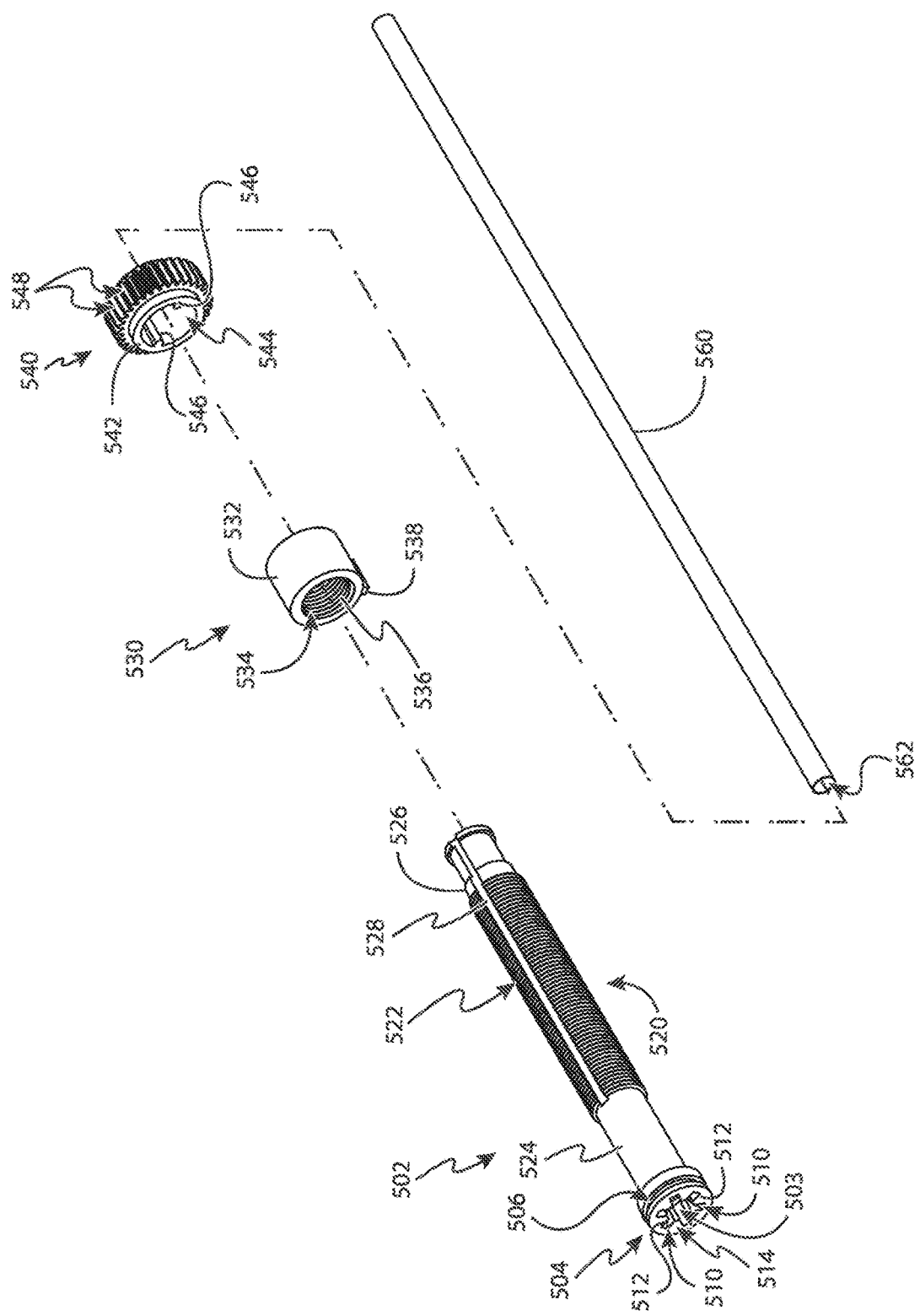
FIG. 6 depicts an exploded perspective view of the cutter actuation assembly of FIG. 5.

Cutter actuation assembly (500) is shown in greater detail in FIGS. 5 and 6. As can be seen, cutter actuation assembly comprises a cutter drive member (502), a translation member (530), a drive gear (540) and a transfer tube (560). Cutter drive member (502) comprises a gate portion (504) and a drive portion (520). As will be described in greater detail below, at least a portion of gate portion (504) is generally configured to couple to at least a portion of gate assembly (600) to communicate rotational and translational motion of cutter drive member (502) to gate assembly (600). As will also be described in greater detail below, at least a portion of gate assembly (600) is coupled to cutter (130) to communicate rotational and translational motion of gate assembly (600) to cutter (130). Thus, it should be understood that rotation and translation of cutter drive member (502) results in corresponding rotation and translation of cutter (130) via the coupling between at least a portion of gate portion (504) and at least a portion of gate assembly (600).

Drive portion (520) of cutter drive member (502) comprises a threaded portion (522) and a longitudinal channel (528) extending axially along cutter drive member (502) through threaded portion (522). Threaded portion (522) is disposed between a distal no-pitch zone (524) and a proximal no-pitch zone (526). As will be described in greater detail below, threaded portion (522) is generally configured to engage with translation member (530) to provide translation of cutter drive member (502). Similarly, longitudinal channel (528) is configured to engage drive gear (540) to provide rotation of cutter drive member (502). As will also be described in greater detail below, each no-pitch zone (524, 526), is configured to permit rotation of cutter drive member (502) without translation of cutter drive member (502).

As best seen in FIG. 6, translation member (530) comprises a cylindrical body (532). Cylindrical body (532) is generally hollow, defining a bore (534) extending axially there through. The interior of bore (534) includes a plurality of threads (536) that are configured to engage threaded portion (522) of cutter drive member (502). As will be described in greater detail below, engagement between threads (536) of translation member (530) and threaded portion (522) of cutter drive member (502) is generally configured to cause translation of cutter drive member (502) in response to rotation of cutter drive member (502).

Translation member (530) further comprises a key feature (538) extending downwardly from body (532). Key feature (538) is configured to be received within at least a portion of outer housing (102) of probe (100). This configuration secures translation member (530) axially and rotatably relative to probe (100). Thus, it should be understood that key feature (538) acts as a mechanical ground for translation member (530). As will be described in greater detail below, this configuration permits translation member (530) to drive translation of cutter drive member (502) relative to probe (100) upon rotation of cutter drive member (502).

Drive gear (540) comprises a cylindrical body (502) that is configured to fit around the outer diameter of cutter drive member (502). Cylindrical body (542) of drive gear (540) is generally hollow, defining a bore (544) extending axially there through. The interior of bore (544) includes a pair of keys (546) extending radially inwardly toward the center of bore (544). As will be described in greater detail below, each key (546) is configured to engage longitudinal channel (528) of cutter drive member (502). Although not shown, it should be understood that cutter drive member (502) includes another substantially identical longitudinal channel (528) on the opposite side of cutter drive member (502) such that both keys (546) are received within a corresponding longitudinal channel (528). As will be understood, this configuration permits drive gear (540) to rotate cutter drive member (502) in response to rotation of drive gear (540).

Drive gear (540) further comprises a plurality of teeth (548) extending outwardly from the exterior of cylindrical body (542). Teeth (548) are configured to engage corresponding teeth (not shown) of a gear (not shown) within holster (200). Although not shown, it should be understood that at least a portion of drive gear (540) extends through an opening in outer housing (102) of probe (100) to permit engagement between drive gear (540) and the corresponding gear of holster (200). As will be described in greater detail below, rotation of drive gear (540) via the gear of holster (200) is generally configured to cause rotation of cutter drive member (502). As will be understood, this rotation of cutter drive member (502) additionally results in simultaneous translation of cutter drive member (502) via translation member (530).

Transfer tube (560) extends from cutter drive member (502) to tissue sample holder (300) to provide communication of tissue samples from cutter drive member (502) to tissue sample holder (300). A lumen (562) is defined within transfer tube (560). A corresponding lumen (503) is extends through cutter drive member (502). Accordingly, it should be understood that lumen (562) of transfer tube (560) and lumen (503) of cutter drive member (502) together define a continuous path for tissue samples to flow through cutter drive member (502) and transfer tube (560) to tissue sample holder (300). As will be described in greater detail below, tissue samples generally flow through cutter (130) into gate assembly (600) and then pass through cutter drive member (502) and transfer tube (560) before finally being deposited within tissue sample holder (300). Thus, it should be understood that both lumen (562) of transfer tube (560) and lumen (503) of cutter drive member (502) are in fluid communication with the interior of cutter (130).

Gate assembly (600) is shown in greater detail in FIGS. 7-11. As will be described in greater detail below, gate assembly (600) is generally configured to temporarily cease progression of tissue samples for visual inspection through sample window (140) of probe (100). Gate assembly (600) comprises a sample inspection member (602), a coupling collar (620), and a gate seal (630) disposed between sample inspection member (602) and cutter drive member (502) of cutter actuation assembly (500). Sample inspection member (602) comprises an inspection portion (604) or window and a gate portion (610). Inspection portion is generally configured as an elongate tube with a lumen (606) extending axially through sample inspection member (602). Sample inspection member (602) of the present example is comprised of a substantially transparent material. Thus, it should be understood that the interior of lumen (606) is visible through inspection portion (604). As will be described in greater detail below, this transparent configuration permits an operator to visually inspect tissue samples as they are received and temporarily stored within inspection portion (604) of sample inspection member (602).

Figure 7:
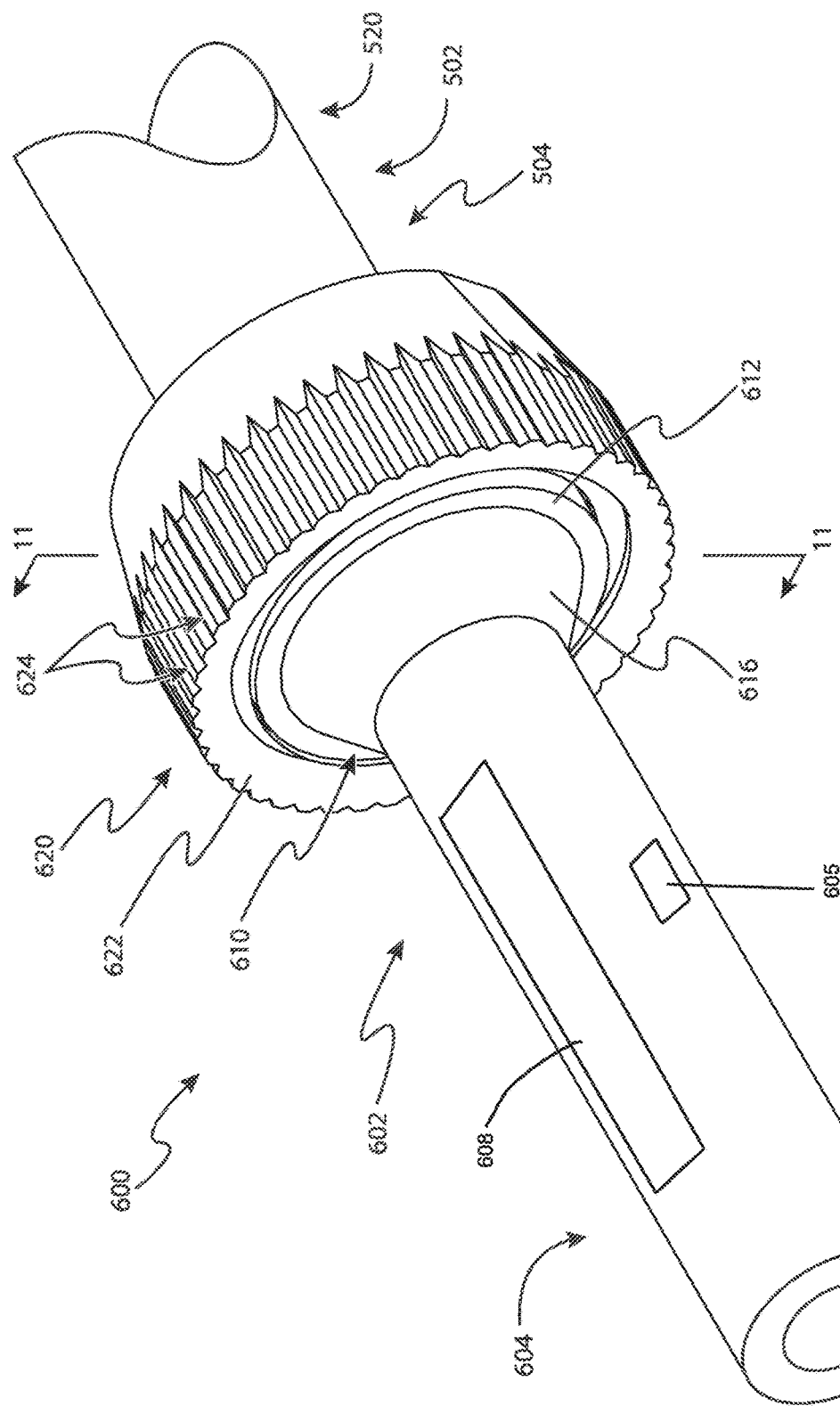
FIG. 7 depicts a perspective view of a gate assembly of the sample acquisition assembly of FIG. 2.

As seen in FIG. 7, inspection portion (604) of sample inspection member (602) is equipped with a sensor (605). Sensor (605) can comprises a variety of sensors such as impedance based sensors, light based sensors, doppler effect sensors, and/or etc. Although not shown, it should be understood that sensor (605) can be in communication with control module or other control features of biopsy device (10) (e.g., circuitry incorporated into holster (200)). In the present example, sensor (605) is generally in communication with lumen (606) to detect the presence of a tissue sample received within sample inspection member (602). In some examples, sensor (605) can be further configured to detect certain characteristics of a tissue sample such as pathogens through impedance based detection mechanisms. In either case, data from sensor (605) can be used to change the operational state of biopsy device (10) when the presence of a tissue sample is detected within sample inspection member (602). For instance, in some examples control circuitry located within biopsy device (10), or associated with biopsy device (10), can stop or reduce the flow of vacuum through sample inspection member (602).

Although sensor (605) of the present example is shown as being associated with inspection portion (604), it should be understood that in other examples sensor (605) can be associated with other components of biopsy device (10). For instance, as described herein inspection portion (604) generally rotates at various stages during operation. Thus, incorporating sensor (605) into inspection portion (604) could present some challenges with coupling sensor (605) to control module or other control features of biopsy device (10). Thus, in other examples it may be desirable to incorporate sensor (605) into certain stationary elements. In some examples this configuration can be implemented by incorporating sensor (605) into outer housing (102) of probe (100). In such a configuration, sensor (605) can be placed in a variety of positions relative to inspection portion (604). For instance, in some examples sensor (605) can be positioned adjacent to inspection portion (604) within sample window (140). In other examples, sensor (605) can be positioned within outer housing (102) distally of inspection portion (604), but proximally of the interface between outer housing (102) and cannula (113) and needle (110). Of course, various other examples involving the placement of sensor (605) can be used as will be appreciated by those of ordinary skill in the art in view of the teachings herein.

As can also be seen in FIG. 7, inspection portion (604) of sample inspection member (602) is further quipped with an access window (608). Access window (608) is generally configured to provide access to the interior of sample inspection member (602). For instance, access window (608) can include a hinged door or other device configured to selectively provide access to the interior of inspection member (602). In some contexts, this may be desirable to permit an operator to remove a tissue sample from sample inspection member (602). For instance, some operators may desire to feel or palpate a tissue sample to obtain some tactile feedback that may be suggestive of the clinical state of the tissue sample. Thus, some operators may desire to remove a tissue sample from sample inspection member (602) rather than just visually inspecting the sample through sample inspection member (602). Although inspection portion (604) of the present example is shown as including access window (608), it should be understood that in other examples access window (608) can be positioned on other components or can be associated with multiple components. Alternatively, in other examples access window (608) can be omitted entirely.

Figure 9:
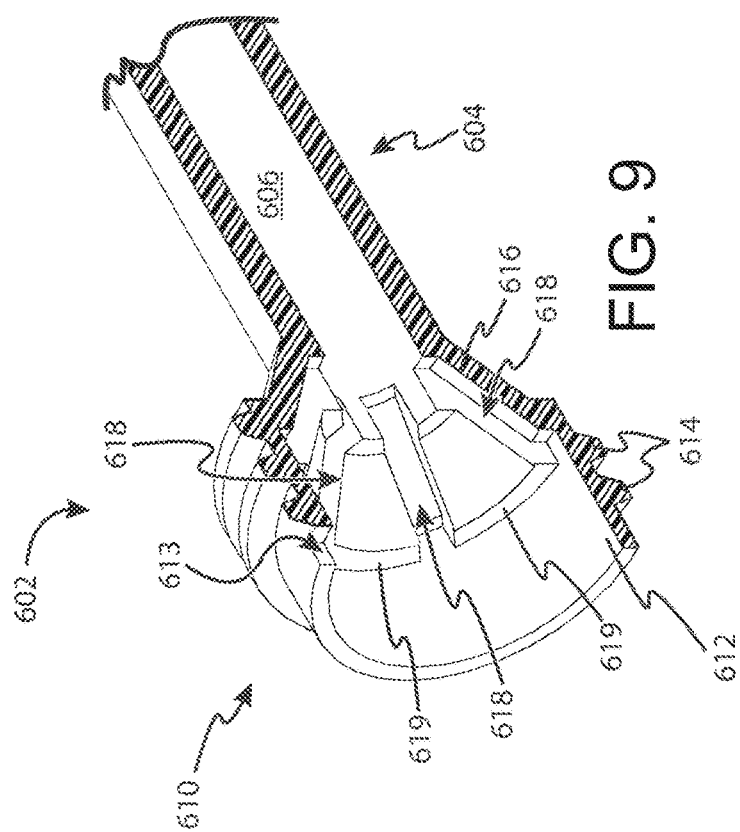
FIG. 9 depicts a perspective cross-sectional view of a sample inspection member of the gate assembly of FIG. 7, the cross-section taken along line 9-9 of FIG. 8.

As best seen in FIG. 9, gate portion (610) of sample inspection member (602) comprises an outer cylindrical wall (612) and a tapered wall (616). Outer cylindrical wall (612) is generally hollow and comprises a diameter that is generally larger than the diameter of inspection portion (604). Thus, as lumen (606) of inspection portion (604) extends into gate portion (610), the diameter of lumen (606) expands in correspondence with the expanded diameter of cylindrical wall (612).

The exterior of cylindrical wall (612) comprises threads (614). Threads (614) extend outwardly from the exterior of cylindrical wall (612). As will be described in greater detail below, threads (614) are generally configured to engage at least a portion of coupling collar (620) to secure sample inspection member (602) to coupling collar (620).

Cylindrical wall (612) further comprises at least one locating feature (613) disposed on the proximal end of cylindrical wall (612). Locating feature (613) is configured to receive at least a portion of cutter drive member (502). As will be described in greater detail below, receipt of at least a portion of cutter dive member (502) within locating feature (613) locks rotational motion of cutter drive member (502) relative to sample inspection member (602). It should therefore be understood that, during use, cutter drive member (502) is configured to communicate rotary motion to sample inspection member (602). This in turn communicates rotary motion to cutter (130).

Because of the expanded diameter of cylindrical wall (612), tapered wall (616) is positioned between inspection portion (604) and cylindrical wall (612). Thus, tapered wall (616) forms a generally frustoconical inner and outer shape to accommodate the transition in diameter from inspection portion (604) to cylindrical wall (612).

The interior of tapered wall (616) defines a plurality of vacuum channels (618) and an inner flange (619). As will be described in greater detail below, vacuum channels (618) are generally configured to permit vacuum to pass through gate seal (630) even with a tissue sample adjacent to gate seal (630). This configuration prevents a pressure differential from forming on either side of gate seal (630). Inner flange (619) is configured to receive at least a portion of gate seal (630). As will be described in greater detail below, gate seal (630) is held in place by compression between inner flange (619) and at least a portion of cutter drive member (502).

Figure 8:
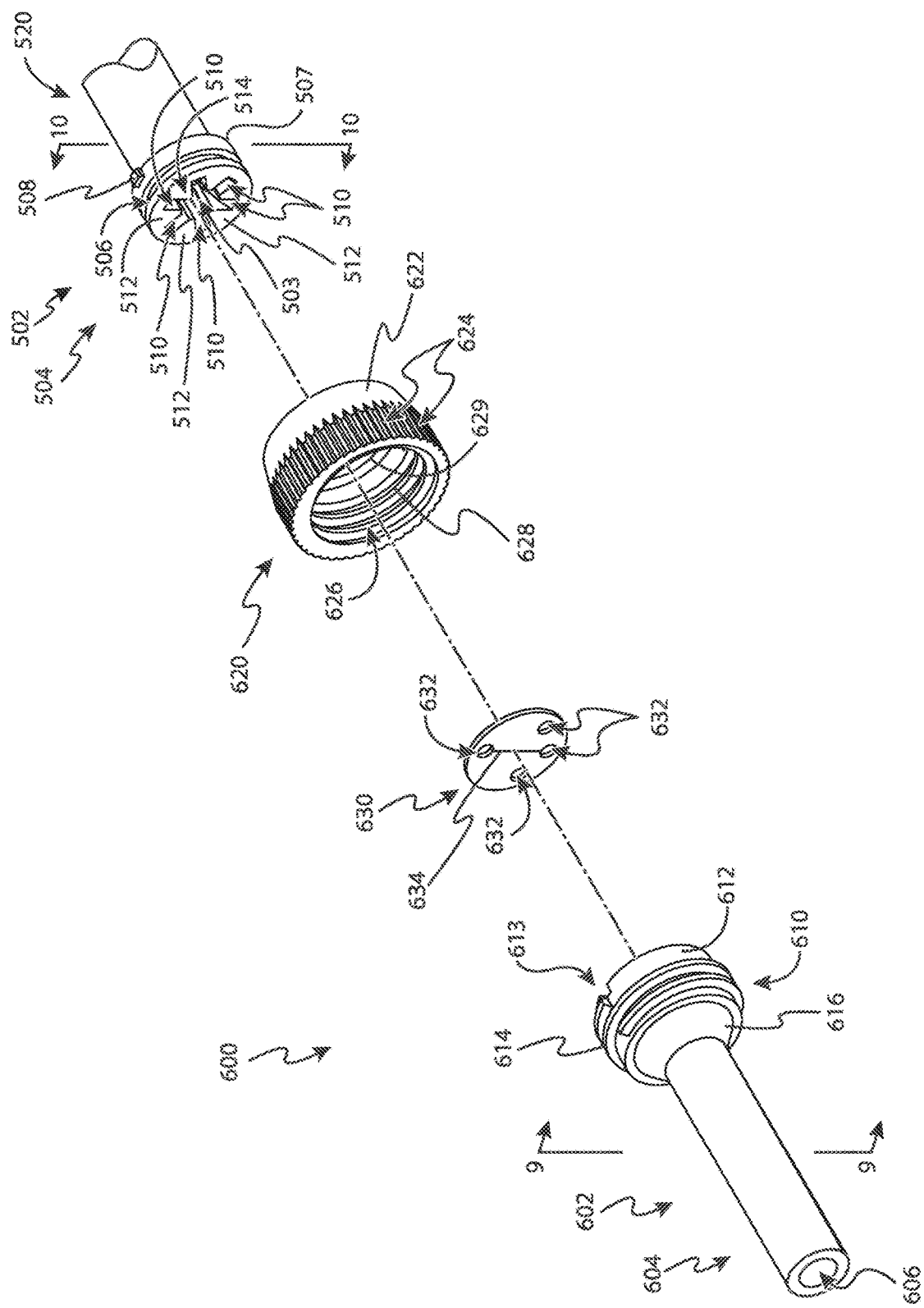
FIG. 8 depicts an exploded perspective view of the gate assembly of FIG. 7.

As best seen in FIG. 8, coupling collar (620) comprises a ring-shaped body (622) with a bore (626) extending axially through body (622). The interior of bore (626) comprises a plurality of threads (628) and a collar (629). Threads (628) are configured to engage corresponding threads (614) of sample inspection member (602) to secure sample inspection member (602) to coupling collar (620). Likewise, and as will be described in greater detail below, collar (629) is configured to engage at least a portion of cutter drive mechanism (502) to axially secure cutter drive mechanism (502) to coupling collar (620).

The exterior of body (622) comprises a plurality of grip features (624) that are recessed into the exterior of body (622). Grip features (624) are generally configured to engage the grip of an operator on coupling collar (620). As will be described in greater detail below, in some circumstances it may be desirable to manually rotate coupling collar (620) relative to sample inspection member (602). Thus, grip features (624) enhance the ability of an operator to rotate coupling collar (620) relative to sample inspection member (602). Although grip features (624) are shown as a series of elongate slots, it should be understood that in other examples any other grip feature can be used as will be apparent to those of ordinary skill in the art in view of the teachings herein.

Gate seal (630) is best seen in FIG. 8. As can be seen, gate seal (630) comprises a generally coin-shaped piece. Gate seal (630) is generally configured to selectively open and close to selectively block a tissue sample from progressing past gate seal (630). Thus, it should be understood that gate seal (630) generally functions to hold a given tissue sample within sample inspection member (602) for visual inspection. Gate seal (630) comprises a plurality of vacuum openings (632) and a gate slit (634). Vacuum openings (632) are configured to permit vacuum to pass through gate seal (630) generally unencumbered, even when a tissue sample is positioned adjacently relative to gate seal (630). Although not shown, it should be understood that in some examples gate seal (630) may also include protrusions or other structural features to maintain some separation between gate seal (630) and any adjacent tissue sample.

Gate slit (634) comprises a slit extending through gate seal (630) from one vacuum opening (632) to another on an opposite side of gate seal (630). Although slit (634) is represented as essentially a line in FIG. 8, it should be understood that gate seal (630) is generally separable at gate slit (634) to transition from a closed position (shown in FIG. 8) to an open position. To permit opening and closing of gate slit (634), gate seal is generally comprised of a flexible elastomeric material such as rubber, silicon, latex, or etc. Although gate seal (630) is generally flexible in nature, it should be understood that gate seal (630) also has some limited rigidity to resiliently bias gate seal (630) toward the closed position shown in FIG. 8.

Figure 10:
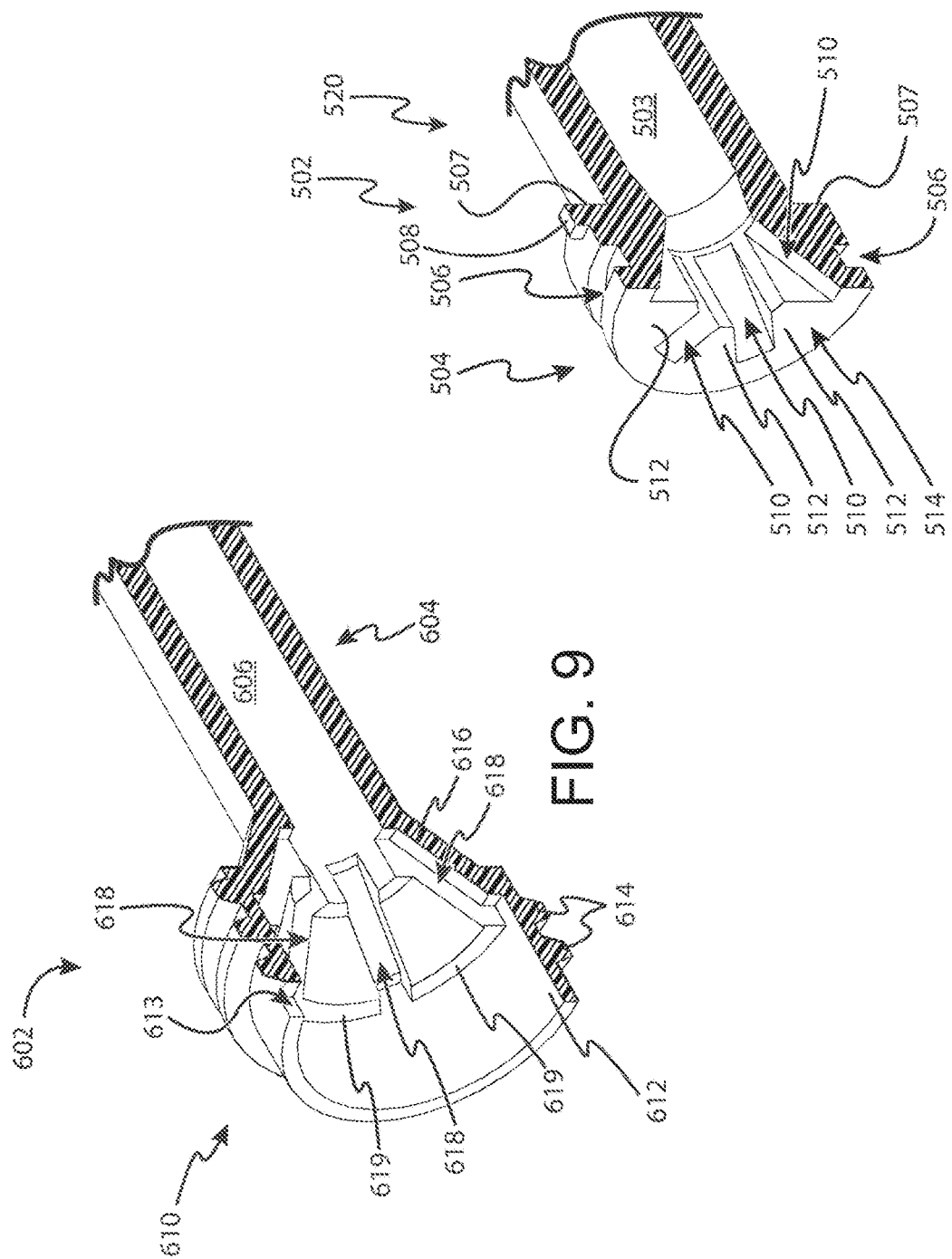
FIG. 10 depicts a perspective cross-sectional view of a cutter drive member of the cutter auction assembly of FIG. 5, the cross-section taken along line 10-10 of FIG. 8.

As described above, cutter drive member (502) includes gate portion (504). Gate portion (504) is best seen in FIG. 10. As will be described in greater detail below, gate portion (504) of cutter drive member (502) is generally configured to abut inner flange (619) of sample inspection member (602) to hold gate seal (630) in position between cutter drive member (502) and sample inspection member (602). The exterior of gate portion (504) comprises a retaining channel (506), a proximal flange (507), and a locating protrusion (508). Retaining channel (506) is configured to receive an o-ring or other sealing feature to substantially seal the interface between cutter drive member (502) and sample inspection member (602). Proximal flange (507) is formed by a differential between the outer diameter of gate portion (504) and drive portion (520) of cutter drive member (502). As will be described in greater detail below, proximal flange (507) is configured to engage collar (629) of coupling collar (620) to permit coupling collar (620) to secure cutter drive member (502) to sample inspection member (602). Similarly, locating protrusion (508) is configured to be received within locating feature (613) of sample inspection member (602) to lock rotation of sample inspection member (602) relative to cutter drive member (502).

The interior of gate portion (504) of cutter drive member (502) comprises a plurality of vacuum channels (510) disposed between a plurality of stop members (512). Both vacuum channels (510) and stop members (512) are disposed angularly around lumen (503) of cutter drive member (502). Vacuum channels (510) are configured to align with corresponding vacuum channels (618) in gate portion (610) of sample inspection member (602). As will be described in greater detail below, when gate seal (630) is disposed between gate portion (504) of cutter drive member (502) and gate portion (610) of sample inspection member (602), respective vacuum channels (510, 618) permit vacuum to flow through vacuum openings (632) of gate seal (630). This configuration permits the flow of vacuum through gate seal (630) even when a tissue sample is positioned adjacent to gate seal (630).

Stop members (512) generally define a common distal face (514) of gate portion (504). As will be described in greater detail below, this common distal face (514) is configured to prevent gate seal (630) from opening proximally into gate portion (504) of cutter drive member (502). Instead, as will also be described in greater detail below, gate seal (630) is configured to open into gate portion (610) of sample inspection member (602).

Stop members (512) also define an inner diameter that generally corresponds to the outer diameter of transfer tube (560) of cutter actuation assembly (500). As described above, transfer tube (560) generally remains stationary as cutter drive member (502) rotates and translates within probe (100). As a consequence of this, transfer tube (560) is configured to pass through the common distal face (514) defined by stop members (512). As will be described in greater detail below, this configuration permits transfer tube (560) to transition gate seal (630) to the open position described above.

Figure 11:
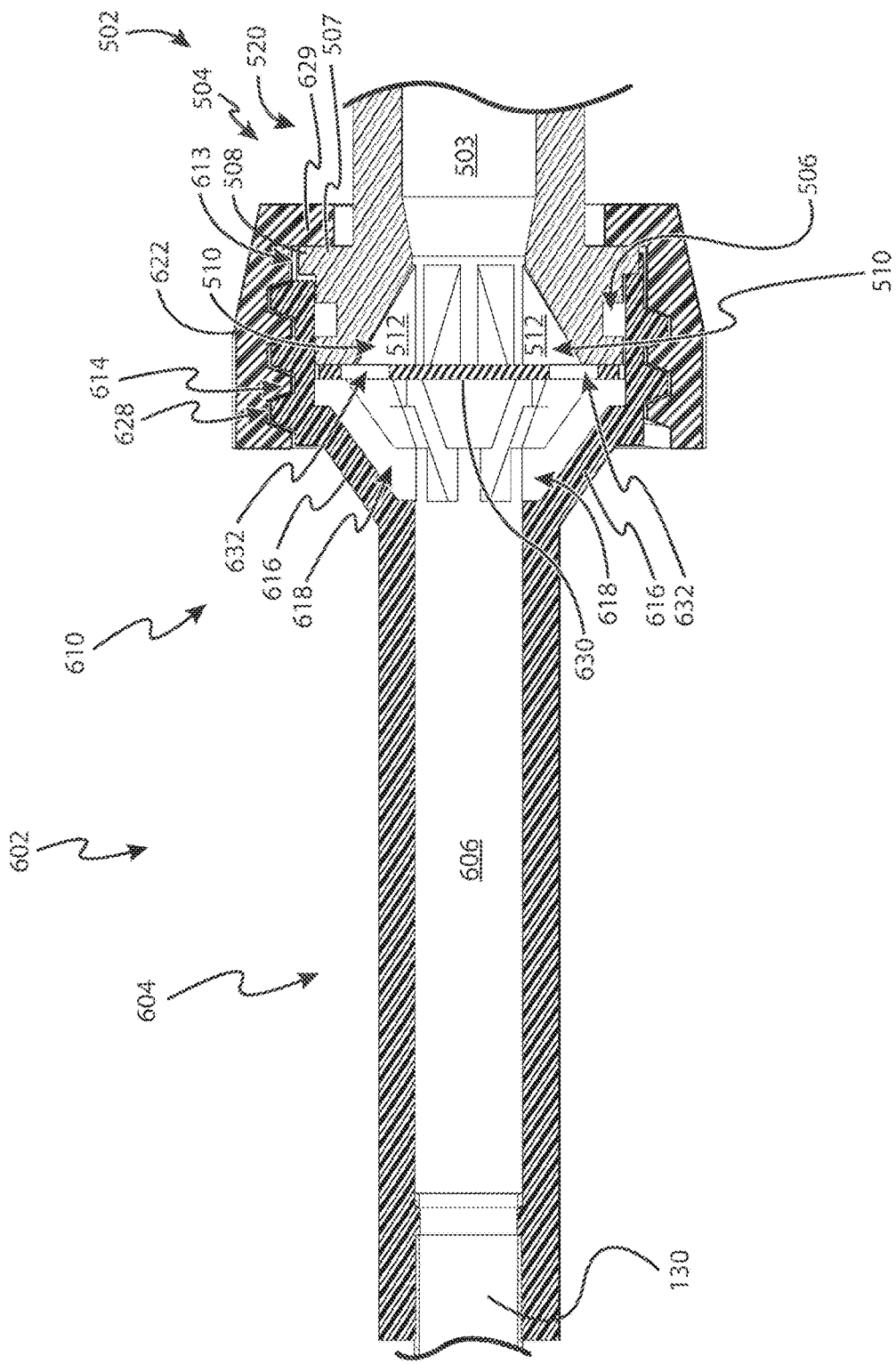
FIG. 11 depicts a cross-sectional view of the gate assembly of FIG. 7, the cross-section taken along line 11-11 of FIG. 7, with the gate assembly in a closed position.

FIG. 11 shows cutter drive member (502) coupled to sample inspection member (602) by coupling collar (620). As can be seen, coupling collar (620) surrounds at least a portion of the exterior of both gate portions (504, 610) of cutter drive member (502) and sample inspection member (602), respectively. Gate portion (504) of cutter drive member (502) is disposed within outer cylindrical wall (612) of sample inspection member (602), with locating protrusion (508) of cutter drive member (502) disposed within locating feature (613) of sample inspection member (602).

Collar (629) of coupling collar (620) engages proximal flange (507) of cutter drive member (502). Correspondingly, threads (614) of sample inspection member (602) engage threads (628) of coupling collar (620). With threads (614) fully engaged with threads (628), collar (629) of coupling collar (620) pulls gate portion (504) of cutter drive member (502) toward gate portion (610) of sample inspection member (602). This in turn holds cutter drive member (502) in the position shown in FIG. 11.

As described above, gate seal (630) is disposed between inner flange (619) of sample inspection member (602) and common distal face of cutter drive member (502) when sample inspection member (602) is coupled to cutter drive member (502). In this position, vacuum channels (510) of cutter drive member (502) and vacuum channels (618) of sample inspection member (602) are aligned with vacuum openings (632) of gate seal (630). Thus, it should be understood that in the configuration shown in FIG. 11, vacuum is free to pass from lumen (503) of cutter drive member (502) through vacuum openings (632) of gate seal (630), through vacuum channels (618) of sample inspection member (602) and into lumen (606) of sample inspection member (602). As described above, this configuration prevents a pressure differential from forming on either side of gate seal (630).

FIGS. 12-18 show an exemplary use of cutter actuation assembly (500) and gate assembly (600) to view a tissue sample through sample window (140) of probe (100). Initially, biopsy device (10) begins with cutter (130) advanced relative to lateral aperture (114) to a distal position such that lateral aperture (114) is in a closed configuration as shown in FIG. 12. With lateral aperture (114) in the closed configuration, an operator can insert needle (110) into the breast of a patient. Insertion of needle (110) can be performed under any one or more of the image guidance modalities described above such as ultrasound, stereotactic x-ray, or MRI.

As best seen in FIG. 13, when cutter (130) is positioned in the distal position, cutter actuation assembly (500) is in a corresponding distal position. When cutter actuation assembly (500) is in the distal position, cutter drive member (502) is positioned distally relative to translation member (530), drive gear (540), and transfer tube (560). As will be understood, translation member (530), drive gear (540), and transfer tube (560) all remain in a stationary axial position as cutter drive member (502) is moved axially to translate cutter (130). Thus, it should be understood that translation member (530), drive gear (540), and transfer tube (560) will remain in the position shown in FIG. 13 as cutter (130) is translated relative to lateral aperture (114) of needle (110).

Figure 15:
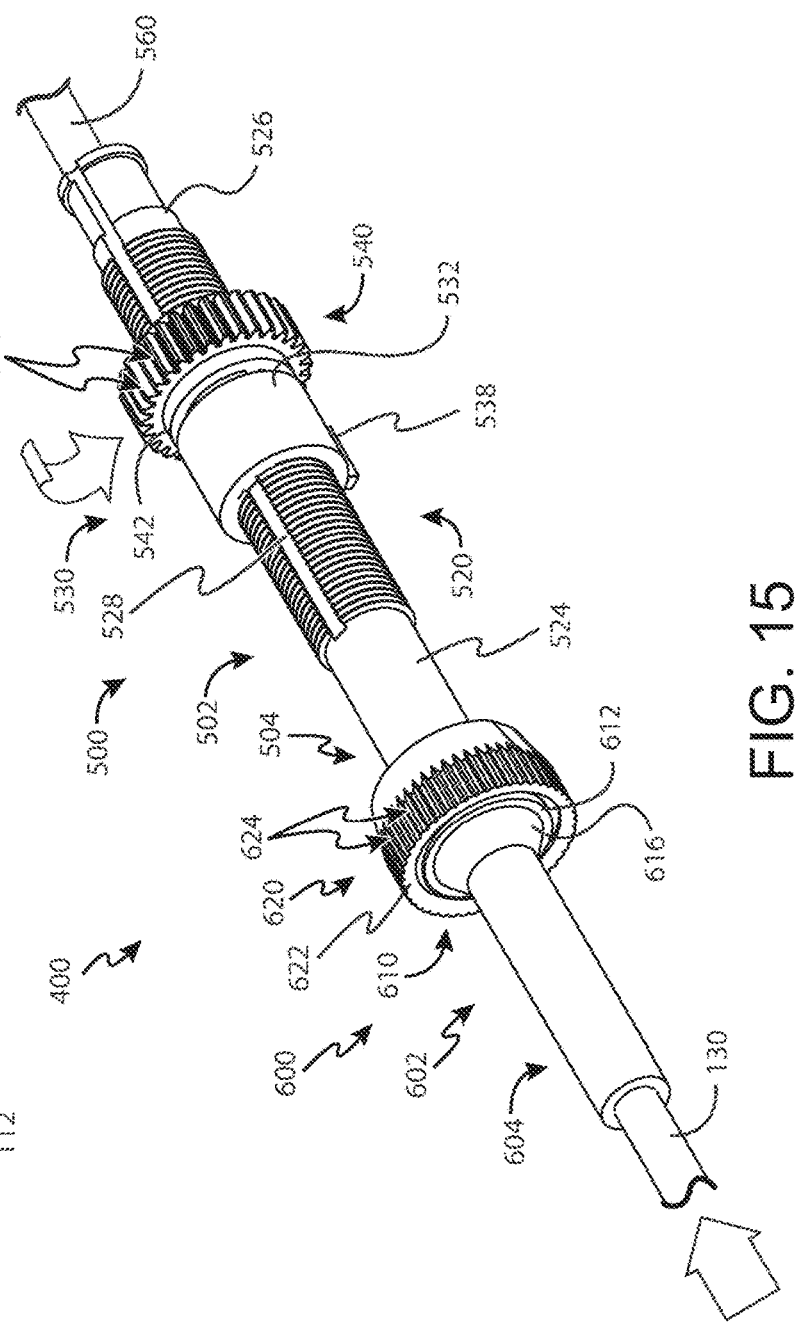
FIG. 15 depicts still another perspective view of the sample acquisition assembly of FIG. 2, with the cutter actuation assembly in an intermediate position.

Once needle (110) is positioned in the patient by an operator as desired, the operator can initiate a sampling sequence. In the present example, biopsy device (10) is configured to receive an operator input via buttons, foot pedals, and/or other features to initiate the sampling sequence. Once the sampling sequence is initiated by an operator, holster (200) will begin to rotate drive gear (540) in a counter clockwise direction as shown in FIG. 15. Keys (546) of drive gear (540) engage longitudinal channels (528) of cutter drive member (502) to initiate rotation of cutter drive member (502) in the counter-clockwise direction. As cutter drive member (502) is rotated, threaded portion (522) of cutter drive member (502) engages threads (536) of translation member (530). Because translation member (530) is rotatably and axially fixed within probe (100), translation member (530) is responsive to counter-clockwise rotation of cutter drive member (502) to provide proximal axial translation of cutter drive member (502) via engagement between threaded portion (522) and threads (536) of translation member (530).

Figure 14:
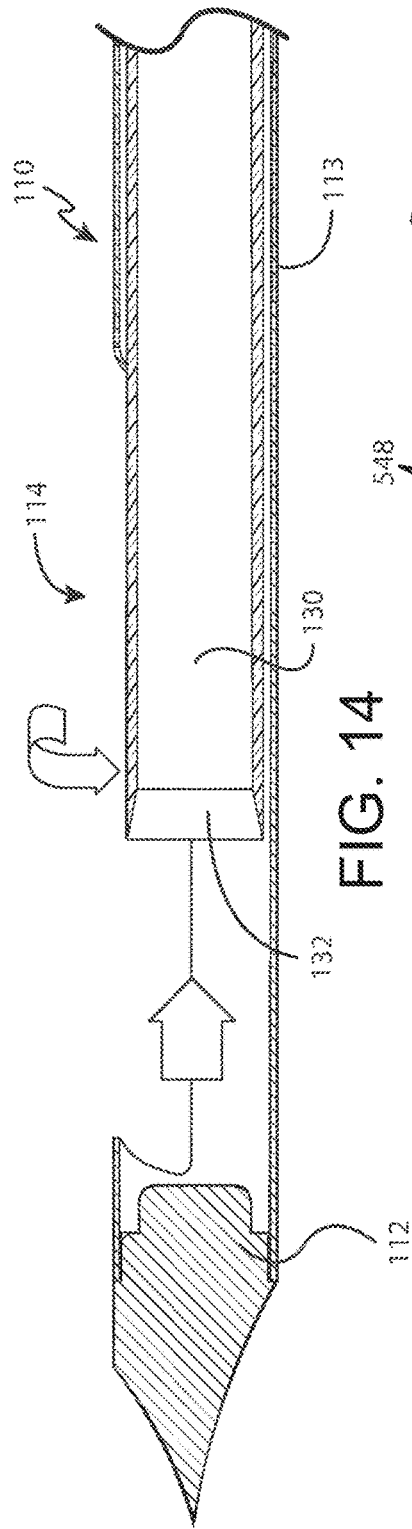
FIG. 14 depicts still another side cross-sectional view of the needle of FIG. 3, the cross-section taken along line 4-4 of FIG. 2, with the cutter in an intermediate position.

Axial translation and rotation of cutter drive member (502) is then transferred to gate assembly (600) by the coupling between sample inspection member (602) and cutter drive member (502) via coupling collar (620). Because cutter (130) is fixedly secured to sample inspection member (602), rotation and translation transferred to sample inspection member (602) is also transferred to cutter (130). Accordingly, as cutter drive member (502) is translated and rotated via drive gear (540) and translation member (530), cutter (130) is correspondingly rotated and translated as shown in FIG. 14.

Figure 16:
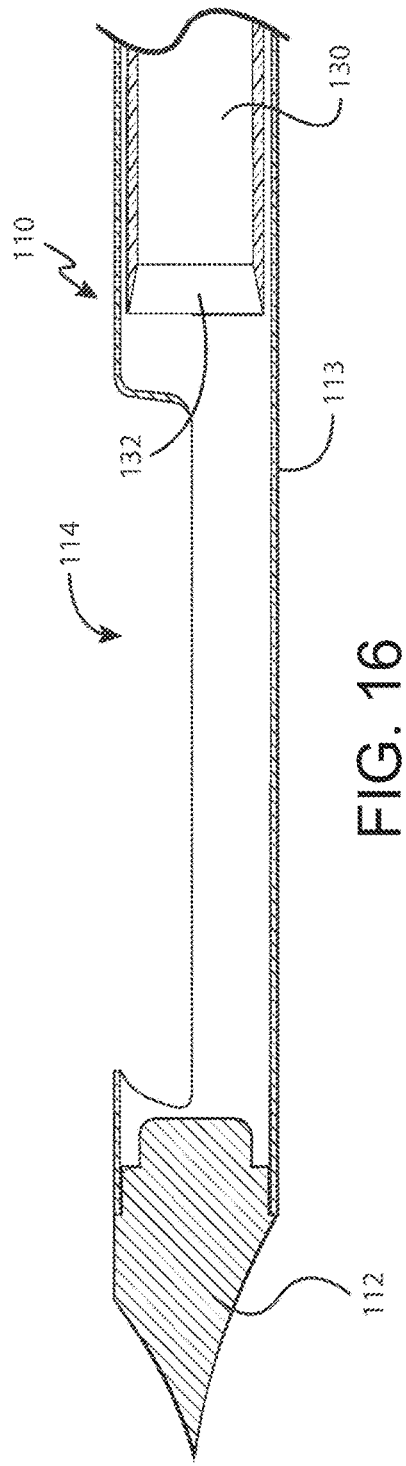
FIG. 16 depicts yet another side cross-sectional view of the needle of FIG. 3, the cross-section taken along line 4-4 of FIG. 2, with the cutter in a proximal position and the lateral aperture in an open configuration.

Rotation and translation of cutter (130) via cutter drive member (502) continues until cutter (130) is positioned at a proximal position as shown in FIG. 16. When cutter (130) is in the proximal position, cutter drive member (502) is correspondingly in a proximal position shown in FIG. 17. When cutter drive member (502) is in the proximal position, cutter drive member (502) is positioned within probe (100) such that translation member (530) and drive gear (540) are positioned proximally relative to threaded portion (522) of cutter drive member (502). At this stage, holster (200) ceases rotation of drive gear (540), which correspondingly ceases rotation and translation of cutter drive member (502).

Figure 17:
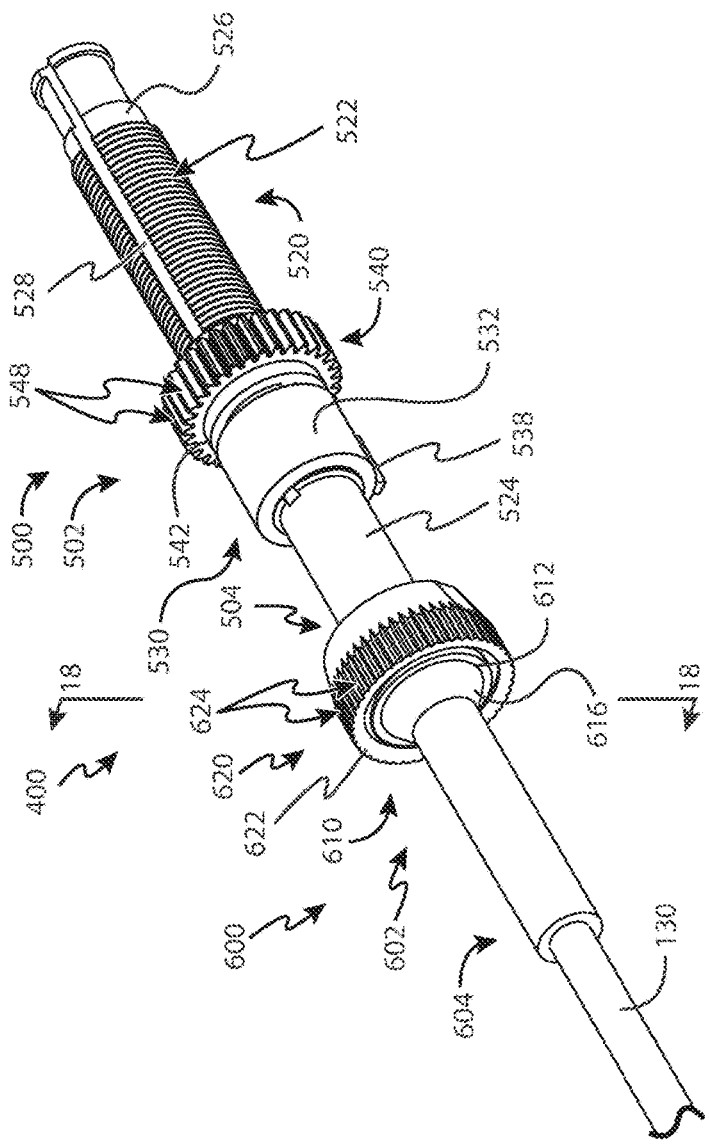
FIG. 17 depicts still another perspective view of the sample acquisition assembly of FIG. 2, with the cutter actuation assembly in a proximal position and the gate assembly in an open position.
Figure 18:
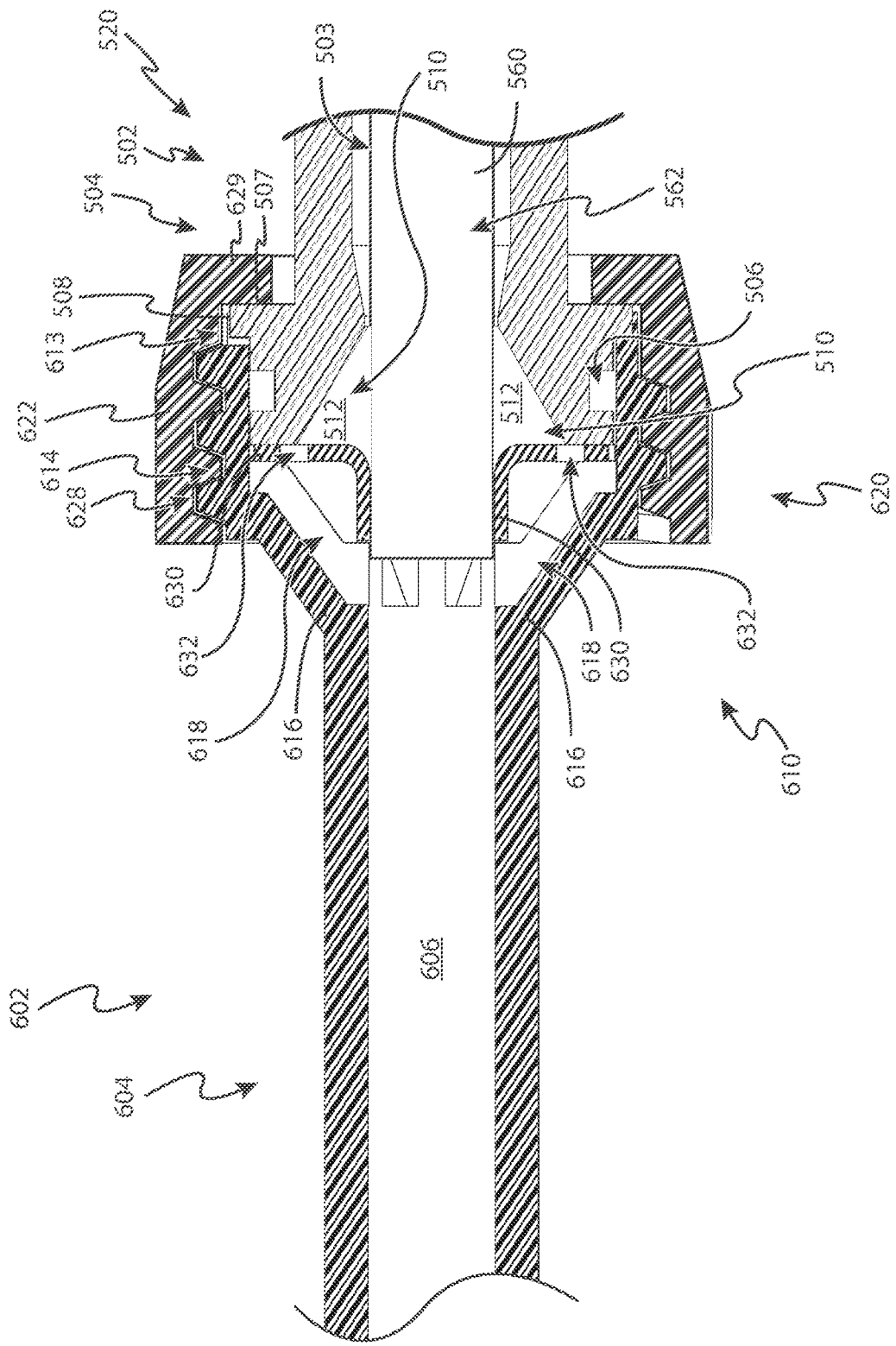
FIG. 18 depicts another side cross-sectional view of the gate assembly of FIG. 7, the cross-section taken along line 11-11 of FIG. 7, with the gate assembly in the open position.

When cutter drive member (502) is in the proximal position shown in FIG. 17, gate assembly (600) is in a corresponding open position. As described above, transfer tube (560) of cutter drive assembly (500) generally remains stationary relative to cutter drive member (502). As best seen in FIG. 18, this configuration results in transfer tube (560) extending through gate seal (630) and into lumen (606) of sample inspection member (602). Because transfer tube (560) extends through gate seal (630), it should be understood that transfer tube (560) engages gate slit (634) to open gate slit (634) around the exterior of transfer tube (560). Thus, when cutter drive member (502) is in the proximal position, gate seal (630) is in an open position. In addition, when cutter drive member (502) is in the proximal position, cutter (130) is positioned in the proximal position such that lateral aperture (114) is in an open position. Accordingly, it should be understood that there is a relationship between gate seal (630) and lateral aperture (114) such that when lateral aperture (114) is in the open position, gate seal (630) is correspondingly in the open position. Likewise, when lateral aperture (114) is in the closed position, gate seal (630) is in a corresponding closed position as shown in FIG. 11.

Once lateral aperture (114) is in the open position, needle (110) is configured so that tissue may be prolapsed within lateral aperture (114). To prolapse tissue within lateral aperture (114), vacuum is applied to cutter (130). In the present example, vacuum is supplied to cutter (130) via tissue sample holder (300). In particular, vacuum is communicated to tissue sample holder (300), which is communicated through transfer tube (560), into lumen (606) of sample inspection member (602) and into cutter (130). Vacuum then pulls tissue through lateral aperture (114). In some examples, vacuum is also applied to lumen (120) of cannula (113) via manifold (116) to assist with prolapsing tissue. Of course, vacuum applied to lumen (120) of cannula (113) via manifold (116) is entirely optional and in some examples vacuum is supplied exclusively through cutter (130).

Once tissue is prolapsed into lateral aperture (114), a tissue sample can be severed via sharp distal edge (132) of cutter (130) by driving cutter (130) distally. To drive cutter (130) distally, holster (200) rotates drive gear (540) in a clockwise direction to initiate the same sequence described above with respect to FIGS. 12-17, but in an opposite direction. As cutter (130) is driven distally by cutter drive member (502), cutter drive member (502) and sample inspection member (602) both move distally such that transfer tube (560) disengages gate seal (630). This causes gate seal (630) to return to the closed position shown in FIG. 11.

With a tissue sample severed by distal translation of cutter (130), the severed tissue sample can next be transported proximally through cutter (130) and into sample inspection member (602). In particular, vacuum is applied to tissue sample holder (300), which flows into lumen (503) of cutter drive member (502) via transfer tube (560). Vacuum then flows through cutter drive member (502) and into lumen (606) of sample inspection member (602) via vacuum channels (510, 618) of cutter drive member (502) and sample inspection member (602) via vacuum openings (632) of gate seal (630). Finally, vacuum flows from lumen (606) of sample inspection member (602) and into cutter (130) to transport the severed tissue sample through cutter (130) and into sample inspection member (602).

Once the severed tissue sample is transported into sample inspection member (602), the severed tissue sample is prevented from traveling further by gate seal (630), which is in the closed position. With the severed tissue sample positioned within sample inspection member (602), an operator can visually inspect the severed tissue sample with the naked eye due to the transparency of sample inspection member (602), which is visible through sample window (140) of probe (100). In some instances, coupling collar (620) may also be used by an operator to manually rotate sample inspection member (602) to provide a 360° view of the severed tissue sample.

Once an operator has completed visual inspection via sample window (140) and sample inspection member (602), the severed tissue sample can be transported to tissue sample holder (300). In particular, the severed tissue sample can be transported to tissue sample holder (300) by returning cutter (130), sample inspection member (602), and cutter drive member (502) to the proximal position shown in FIGS. 16-18. As described above, this causes sample inspection member (602) and cutter drive member (502) to translate relative to transport tube (560) to position transfer tube (560) through gate slit (634) in gate seal (630) so that gate seal (630) is in the open position. With gate seal (630) in the open position, the severed tissue sample can be freely transported into transfer tube (560), through gate seal (630), and into tissue sample holder (300). At this stage, cutter (130) is also positioned in the proximal position so that lateral aperture (114) is in the open position. Accordingly, transporting the severed tissue sample to tissue sample holder (300) also prepares needle (110) for receipt of another tissue sample holder.

With the severed tissue sample received in tissue sample holder (300) an operator can next proceed by collecting one or more additional samples using the process described above with respect to the severed tissue sample. After collecting any suitable number of tissue samples, an operator may finalize the procedure by removing needle (110) from the patient, optionally marking the biopsy site, and sealing the opening in the patient. Any number of tissue samples collected during the biopsy procedure can finally be removed from tissue sample holder (300) and subjected to any desired tissue sample analysis procedure.

III. BIOPSY DEVICE WITH EXEMPLARY ALTERNATIVE CUTTER ACTUATION ASSEMBLY

Figure 19:
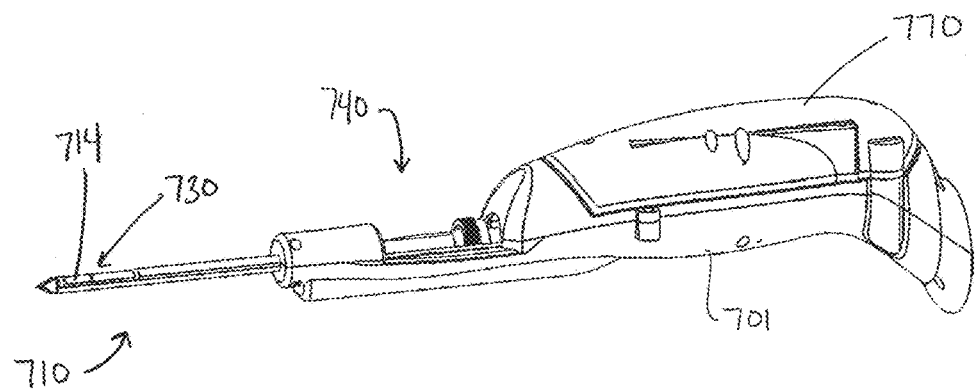
FIG. 19 depicts a perspective view of an exemplary alternative biopsy device.

FIG. 19 shows an exemplary alternative biopsy device (700) that is configured and operable just like biopsy device

(10) described above except for the differences explicitly noted herein. Biopsy device (700) comprises a cutter (730), a lateral aperture (714), and a needle (710) extending distally from a probe (701). It should be understood that cutter (730), lateral aperture (714), needle (710) and probe (701) function substantially similar to cutter (130), lateral aperture (114), needle (110) and probe (100), respectively, described above. Biopsy device (700) further comprises a holster (770) that is configured and operable just like holster (200) described above, except as otherwise described below. Holster (770) is configured to couple with probe (701). As will be described in greater detail below, holster (770) comprises a motor gear (780) and a motor (790) enclosed within the housing of holster (770) and mutually operable to provide power and/or movement to the components of probe (701). Although not shown, it should be understood that a tissue sample holder, similar to tissue sample holder (300) described above, may be coupled to a proximal end of probe (701) to receive tissue samples cut by cutter (730).

As further seen in FIG. 19, probe (701) defines a sample window (740) disposed proximally adjacent to the proximal end of needle (710). Similar to sample window (140) of biopsy device (10) described above, sample window (740) is configured to permit an operator to visualize individual tissue samples as they are collected via needle (710) to thereby permit an operator to visually inspect a severed tissue sample prior to transportation of the severed tissue sample to tissue sample holder (300).

Figure 20:
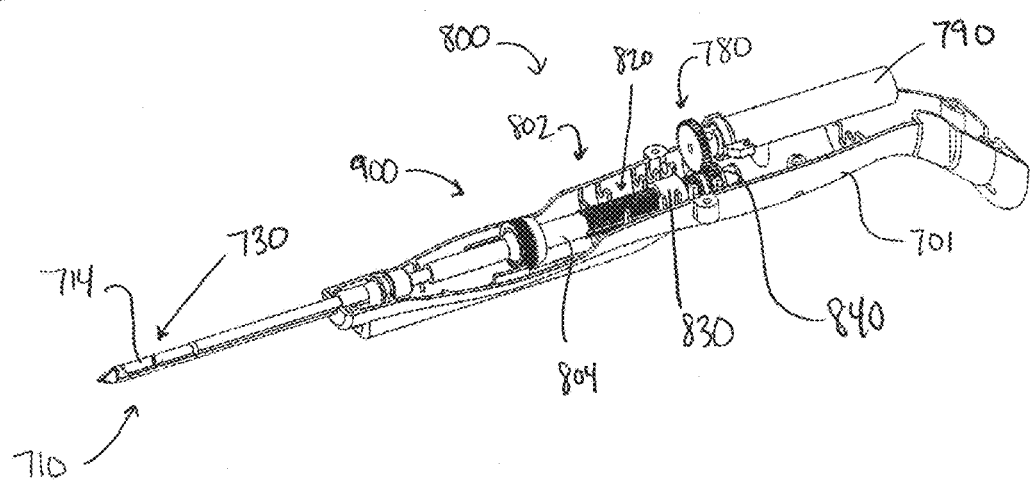
FIG. 20 depicts a perspective cutaway view of a probe of the biopsy device of FIG. 19.

Biopsy device (700) further comprises an exemplary cutter auction assembly (800) enclosed within probe (701), as seen in FIG. 20. Cutter actuation assembly (800) comprises a cutter drive member (802), a translation member (830), and a drive gear (840). Similar to cutter drive member (502) described above, cutter drive member (802) includes a gate portion (804) and a drive portion (820). As will be described in greater detail below, at least a portion of gate portion (804) is configured to couple to at least a portion of a gate assembly (900) to communicate rotational and translation motion of cutter drive member (802) to gate assembly (900). As will also be described in greater detail below, at least a portion of gate assembly (900) is coupled to cutter (730). Thus, it should be understood that rotation and translation of cutter drive member (802) results in corresponding rotation and translation of cutter (730) via the coupling between at least a portion of gate portion (804) and at least a portion of gate assembly (900).

Figure 21:
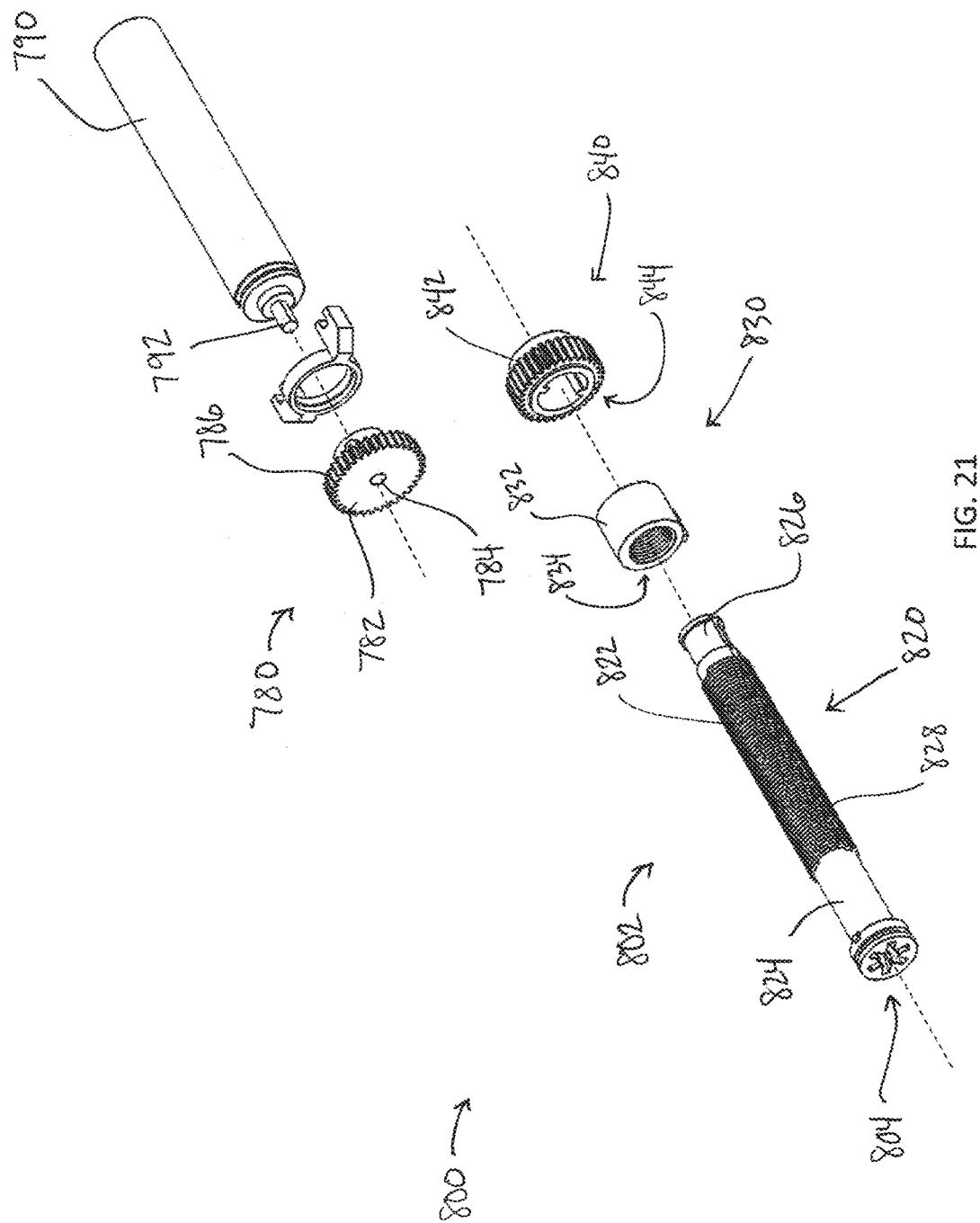
FIG. 21 depicts a perspective exploded view of a cutter actuation assembly of the probe of FIG. 20.

As best seen in FIG. 21, drive portion (820) of cutter drive member (802) comprises a threaded portion (822) and a pair of longitudinal channels (828) extending axially along cutter drive member (802) through threaded portion (822). Threaded portion (822) is disposed between a distal no-pitch zone (824) and a proximal no-pitch zone (826). As will be described in greater detail below, threaded portion (822) is generally configured to engage with translation member (830) to provide translation of cutter drive member (802). Similarly, longitudinal channels (828) are configured to engage drive gear (840) to provide rotation of cutter drive member (802). As will be described in greater detail below, each no-pitch zone (824, 826) is configured to permit rotation of cutter drive member (802) without translation of cutter drive member (802).

Translation member (830) comprises a cylindrical body (832) that is generally hollow and defines a bore (834) extending axially through body (832). The interior of bore (834) includes a threading (836) that is configured to engage threaded portion (822) of cutter drive member (802). As will be described in greater detail below, engagement between threading (836) of translation member (830) and threaded portion (822) of cutter drive member (802) is generally configured to cause translation of cutter drive member (802) in response to rotation of cutter drive member (802). In the present example, threading (836) is shown as including only a single turn of threading such that threading (836) may be characterized as only having a single thread. In some contexts, this configuration may be desirable to more readily manufacture translation member (830) using injection molding based manufacturing operations. However, it should be understood that in other examples threading (836) can include multiple threads extending along the entire, or a portion of, the axial length of translation member (830).

Figure 22:
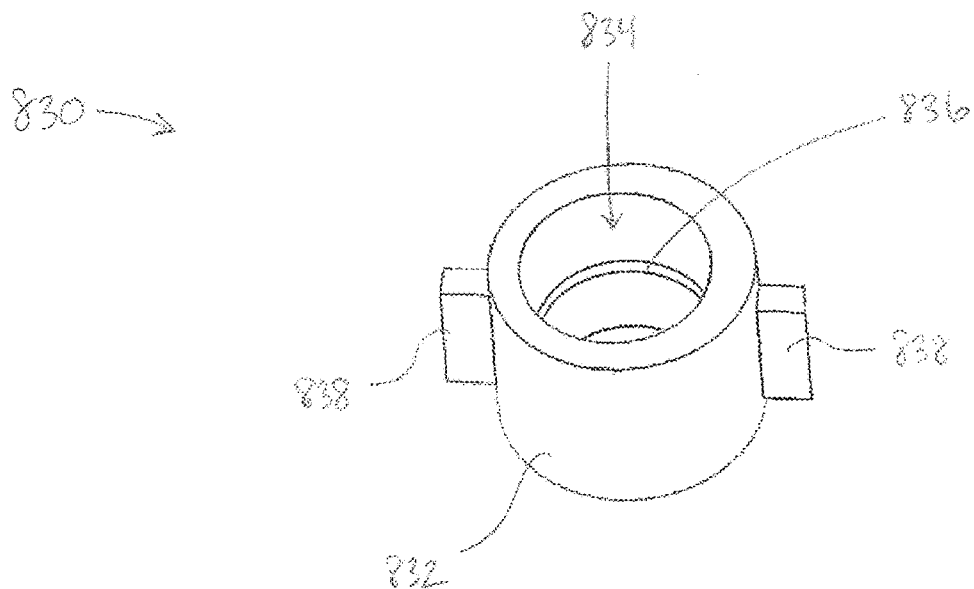
FIG. 22 depicts a perspective view of a translation member of the cutter actuation assembly of FIG. 21.
Figure 23:
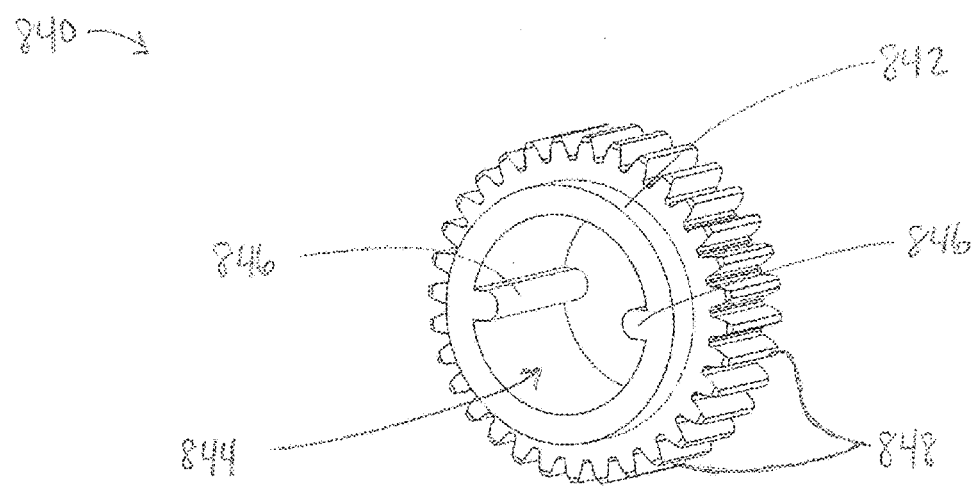
FIG. 23 depicts a perspective view of a drive gear of the cutter actuation assembly of FIG. 21.

Translation member (830) further comprises a pair of key features (838) extending upwardly and downwardly from body (832), as best seen in FIG. 22. Key features (838) are configured to be received within at least a portion of probe (701) to thereby secure translation member (830) axially and rotatably relative to probe (701). It should be understood that key features (838) serves as a mechanical ground for translation member (830). As will be described in greater detail below, this configuration permits translation member (830) to drive translation of cutter drive member (802) relative to probe (701) upon rotation of cutter drive member (802).

Figure 25:
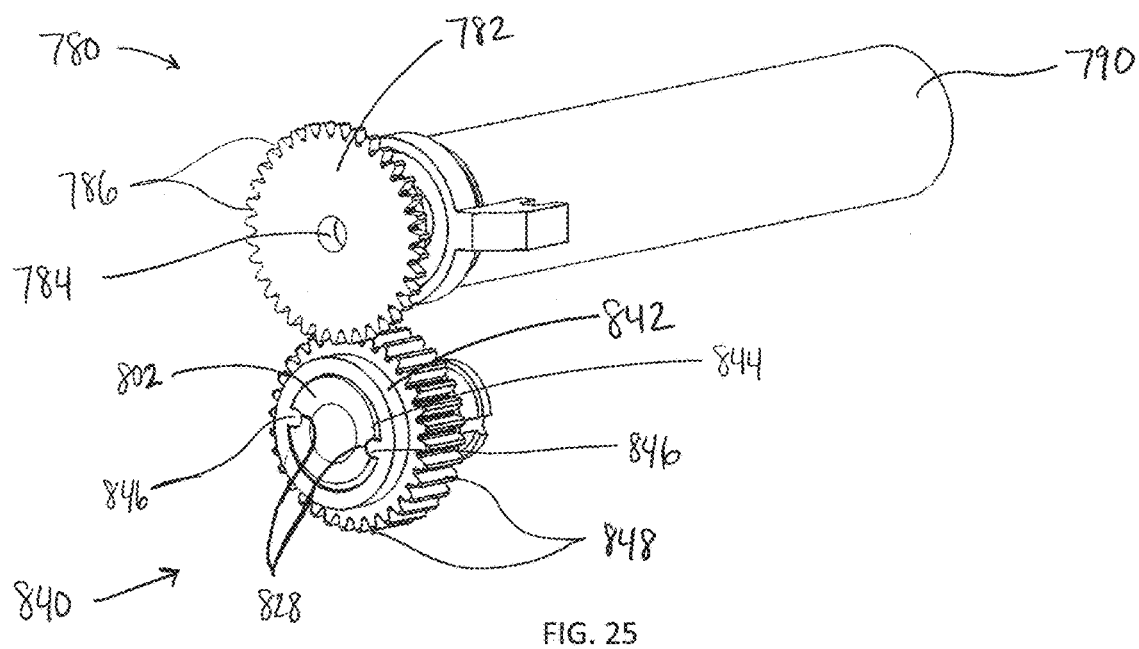
FIG. 25 depicts a partial perspective view of the cutter actuation assembly of FIG. 21.

Drive gear (840) comprises a cylindrical body (842) that is configured to fit around the outer diameter of cutter drive member (802). Cylindrical body (842) of drive gear (840) is generally hollow, defining a bore (844) extending axially therethrough. The interior of bore (844) includes a pair of keys (846) extending radially inwardly toward the center of bore (844). As will be described in greater detail below, each key (846) is configured to engage longitudinal channel (828) of cutter drive member (802). As best seen in FIG. 25, it should be understood that cutter drive member (802) includes another substantially identical longitudinal channel (828) on the opposite side of cutter drive member (802) such that both keys (846) of drive gear (840) are received within a corresponding longitudinal channel (828). As will be understood, this configuration permits drive gear (840) to rotate cutter drive member (802) in response to rotation of drive gear (840).

Drive gear (840) further comprises a plurality of teeth (848) extending outwardly from the exterior of cylindrical body (842). As will be described in greater detail below, teeth (848) are configured to engage corresponding teeth (786) of a motor gear (780) enclosed within holster (770). Although not shown, it should be understood that at least a portion of drive gear (840) extends through an opening in the outer housing of probe (701) to permit engagement between drive gear (840) and the corresponding motor gear (780) of holster (770). As will be described in greater detail below, rotation of drive gear (840) is provided via the rotation of motor gear (780) of holster (770), which thereby generally causes rotation of cutter drive member (802). As will be understood, this rotation of cutter drive member (802) additionally results in simultaneous translation of cutter drive member (802) via translation member (830).

Motor (790) of holster (770) is configured to drive various components of probe (701), particularly the components of cutter actuation assembly (800) described above. Motor (790) is fully enclosed within the housing of holster (770). To communicate the power of motor (790) to probe (701), holster (770) includes motor gear (780) that is operably coupled to motor (790), as seen in FIG. 20. Motor gear (780) comprises a cylindrical body (782) that is configured to fit around a rotatable engagement feature (792) that extends proximally from motor (790). In particular, cylindrical body (782) of motor gear (780) is generally hollow, defining a bore (784) extending axially therethrough. The interior of bore (784) is sized and shaped to correspond to the profile of rotatable engagement feature (792) of motor (790) such that bore (784) is configured to securely receive rotatable engagement feature (792) therein. Rotatable engagement feature (792) is operable to rotate relative to motor (790) in response to the activation of motor (790). In this instance, with rotatable engagement feature (792) coupled to bore (784) of motor gear (780), motor (790) is operable to cause rotation of motor gear (780) through the rotation of rotatable engagement feature (792).

Figure 24:
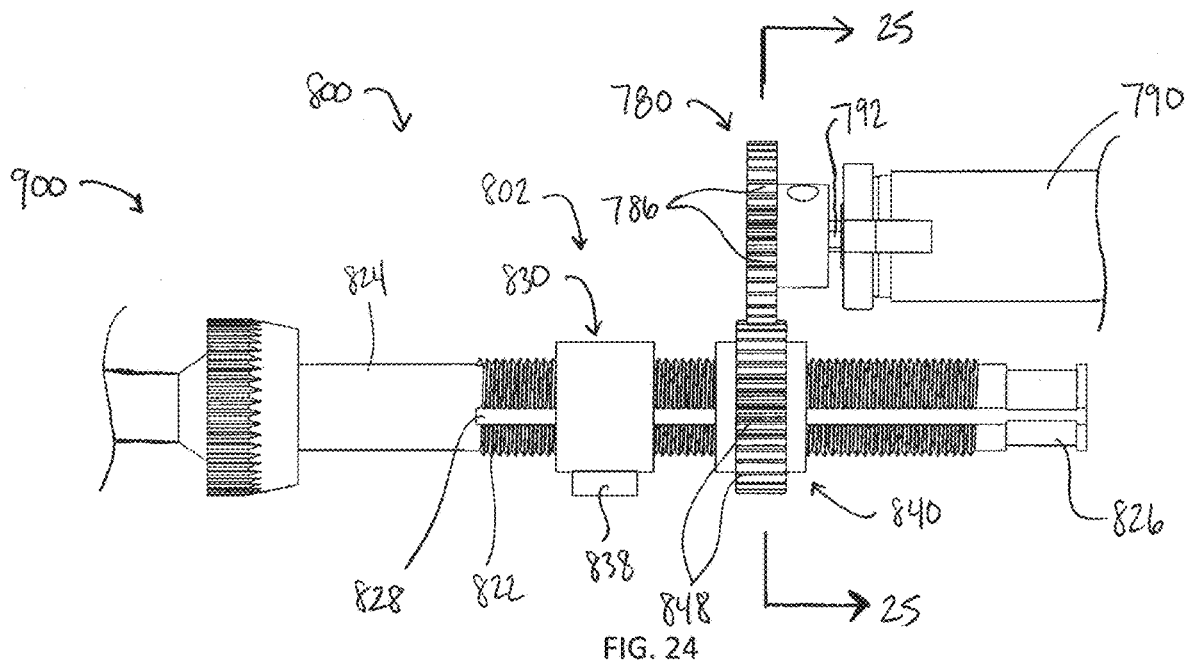
FIG. 24 depicts side elevational view of the cutter actuation assembly of FIG. 21.

Motor gear (780) further includes a plurality of teeth (786) extending outwardly from the exterior of cylindrical body (782), as best seen in FIG. 21. Motor gear (780) is partially enclosed within the housing of holster (770) and at least partially extending into probe (701) to thereby engage drive gear (840). In particular, as seen in FIG. 20, motor gear (780) is positioned within holster (770) at a longitudinal position that aligns with the position of drive gear (840) within probe (701) when holster (770) is coupled to probe (701). In this instance, as further seen in FIG. 24, teeth (786) of motor gear (780) extend into probe (701) and mesh with teeth (848) of drive gear (840) such that rotation of motor gear (780), powered by motor (790), causes corresponding rotation of drive gear (840). Similar to drive gear (540) described above, rotation of drive gear (840) is operable to drive cutter actuation assembly (800) in probe (701).

Although not shown, it should be understood that cutter actuation assembly (800) may further comprise a transfer tube as similarly described above. In this instance, the transfer tube extends from cutter drive member (802) to tissue sample holder (300) to provide communication of tissue samples from cutter drive member (802) to tissue sample holder (300). Similar to transfer tube (560) described above, a lumen may be defined within the transfer tube to communicate with a corresponding lumen of cutter drive member (802). Accordingly, it should be understood that the lumen of the transfer tube and the lumen of cutter drive member (802) together define a continuous path for tissue samples to flow through cutter drive member (802) and the transfer tube to tissue sample holder (300). As will be described in greater detail below, tissue samples generally flow through cutter (730) into gate assembly (900) and then pass through cutter drive member (802) and the transfer tube before finally being deposited within tissue sample holder (300). Thus, it should be understood that both the lumen of the transfer tube and the lumen of cutter drive member (802) are in fluid communication with the interior of cutter (730).

Gate assembly (900) of the present example is configured and operable just like gate assembly (600) described above, except that gate assembly (900) is disposed distally to cutter drive member (802) rather than cutter drive member (502) of cutter actuation assembly (500). In other words, it should be understood that gate assembly (900) functions substantially similar to gate assembly (600) described above except for that gate assembly (900) is configured to receive at least a portion of cutter drive member (802) of cutter actuation assembly (800) to thereby lock rotational motion of cutter drive member (802) relative to gate assembly (900). As seen in FIG. 20, similar to gate assembly (600), gate assembly (900) is generally configured to temporarily cease progression of tissue samples for visual inspection through same window (740) of probe (701). Gate assembly (900) comprises a sample inspection member (902), a coupling collar (920), and a gate seal (not shown) disposed between sample inspection member (902) and cutter drive member (802) of cutter actuation assembly (800). It should be understood that sample inspection member (902), coupling collar (920), and the gate seal are configured and operable similar to sample inspection member (602), coupling collar (620) and gate seal (630), respectively, described above. It should therefore be understood that, during use, cutter drive member (802) is configured to communicate rotary motion to sample inspection member (902) of gate assembly (900), which in turn communicates rotary motion to cutter (730).

Figure 26A:
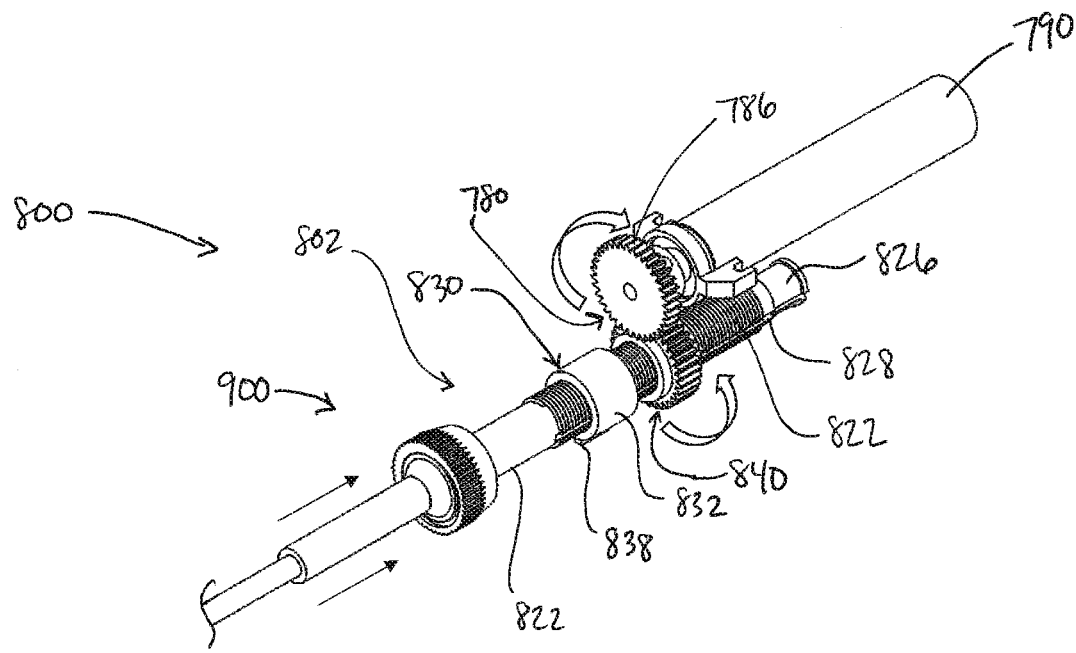
FIG. 26A depicts a perspective view of the cutter actuation assembly of FIG. 21, with the cutter actuation assembly in a proximal position.
Figure 26B:
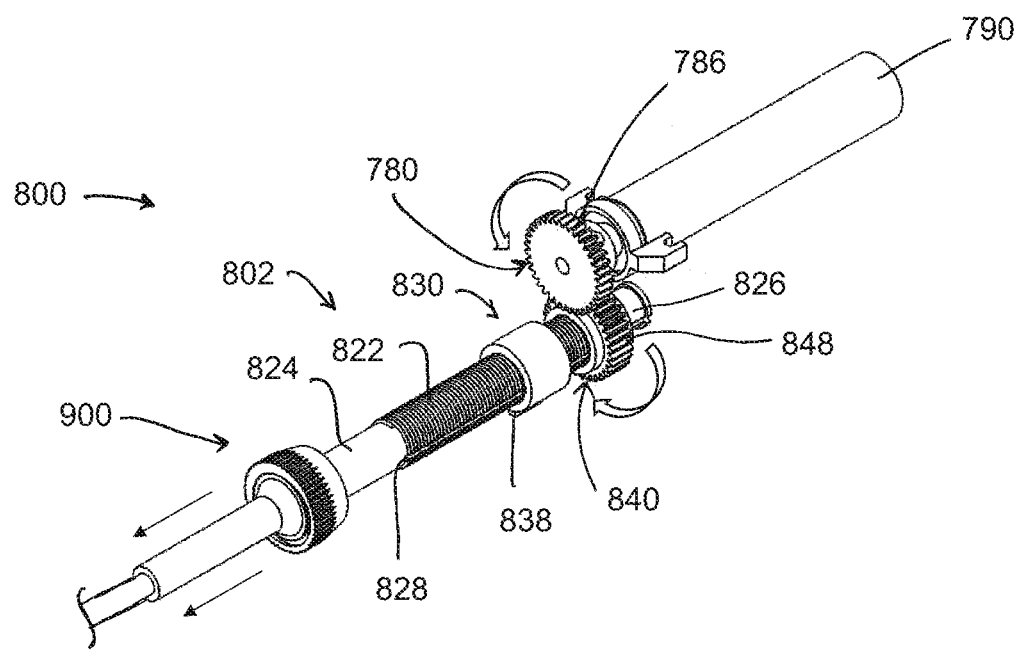
FIG. 26B depicts another perspective view of the cutter actuation assembly of FIG. 21, with the cutter actuation assembly in a distal position.
Figure 27A:
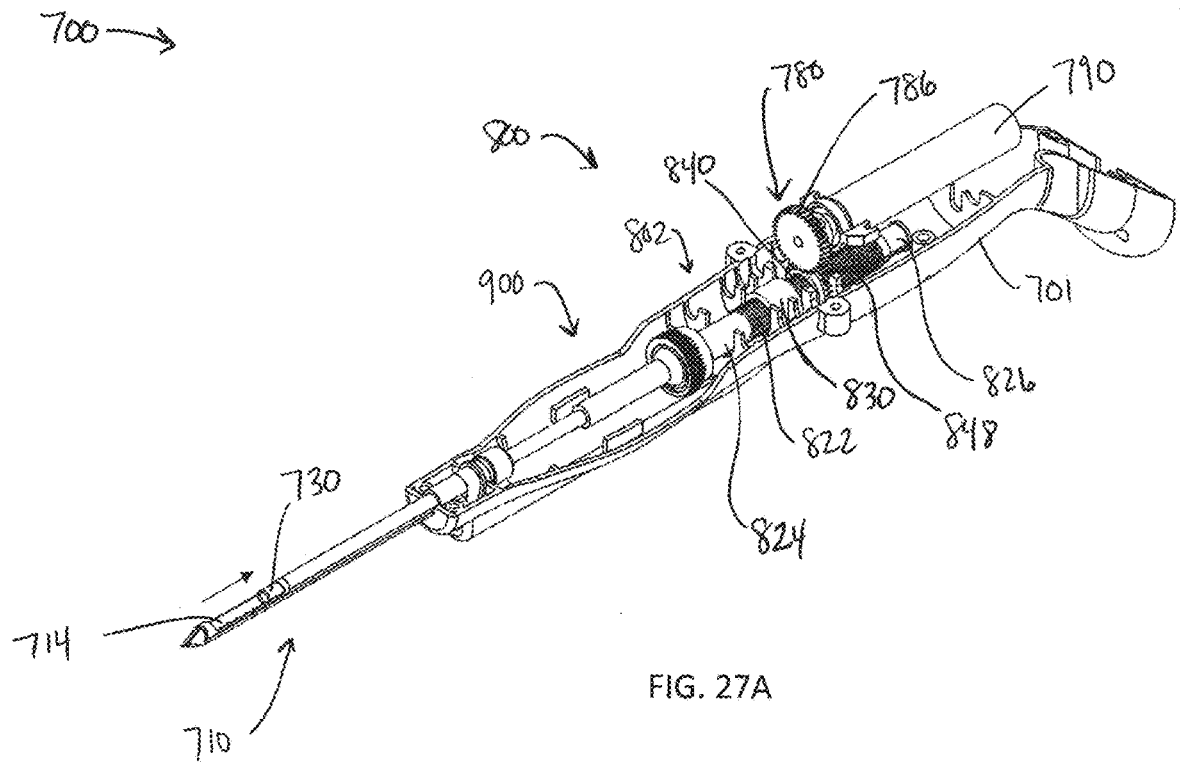
FIG. 27A depicts another perspective cutaway view of the probe of FIG. 20, with the cutter actuation assembly in the proximal position.
Figure 27B:
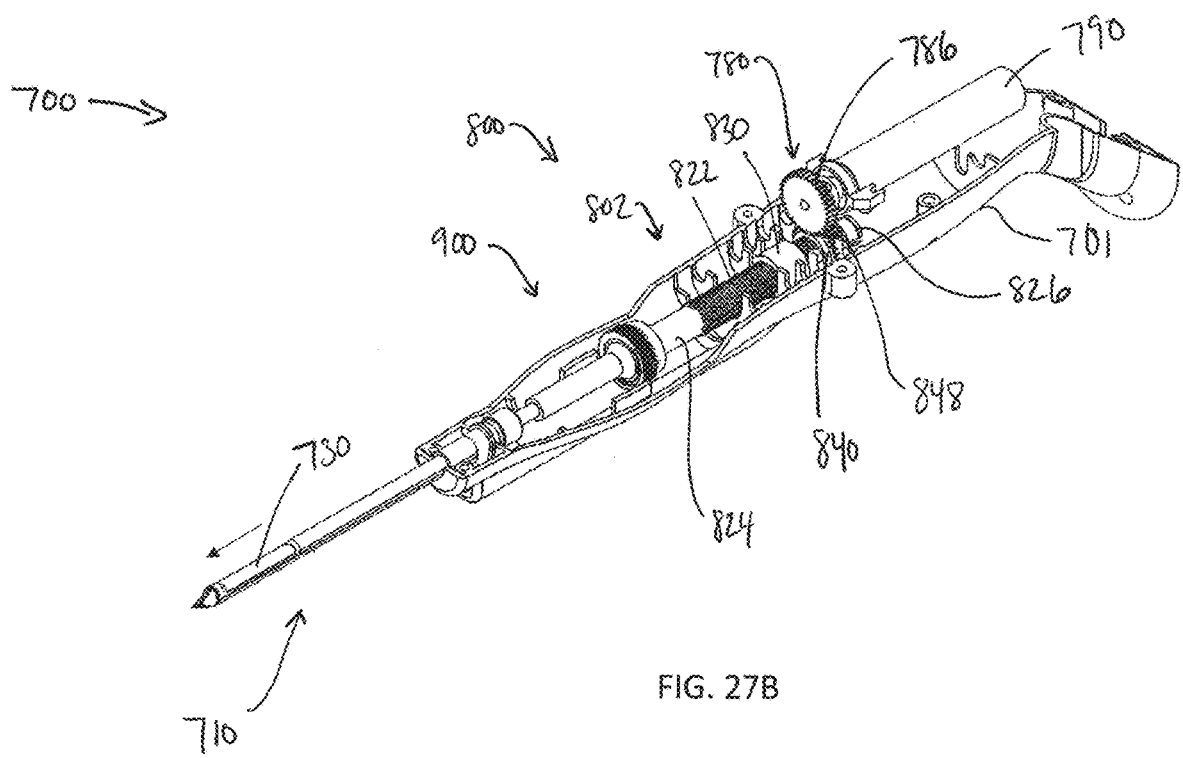
FIG. 27B depicts still another perspective cutaway view of the probe of FIG. 20, with the cutter actuation assembly in the distal position.

FIGS. 26-27 show an exemplary use of cutter actuation assembly (800) and gate assembly (900). Initially, biopsy device (700) begins with cutter (730) advanced relative to lateral aperture (714) to a distal position such that lateral aperture (714) is in a closed configuration as shown in FIG. 27B. With lateral aperture (714) in the closed configuration, an operator can insert needle (710) into the breast of a patient. Insertion of needle (710) can be performed under any one or more of the image guidance modalities described above such as ultrasound, stereotactic x-ray, or MRI.

As best seen in FIG. 26B, when cutter (730) is positioned in the distal position, cutter actuation assembly (800) is in a corresponding distal position. When cutter actuation assembly (800) is in the distal position, cutter drive member (802) is positioned distally relative to translation member (830) and drive gear (840). As will be understood, translation member (830) and drive gear (840) all remain in a stationary axial position as cutter drive member (802) is moved axially to translate cutter (730). Thus, it should be understood that translation member (830) and drive gear (840) will remain in the position shown in FIG. 26B as cutter (730) is translated relative to lateral aperture (714) of needle (710).

Once needle (710) is positioned in the patient by an operator as desired, the operator can initiate a sampling sequence. In the present example, biopsy device (700) is configured to receive an operator input via buttons, foot pedals, and/or other features to initiate the sampling sequence. Once the sampling sequence is initiated by an operator, motor (790) is activated to rotate rotatable engagement feature (792) in a clockwise direction. In this instance, with motor gear (780) coupled to rotatable engagement feature (792), motor gear (780) similarly rotates in the clockwise. With teeth (786) of motor gear (780) meshed with teeth (848) of drive gear (840), the rotation of motor gear (780) causes the simultaneous rotation of drive gear (840) in an opposite, counterclockwise direction, as seen in FIG. 26B. Keys (846) of drive gear (840) engage longitudinal channels (828) of cutter drive member (802) to initiate rotation of cutter drive member (802) in the counterclockwise direction. As cutter drive member (802) is rotated, threaded portion (822) of cutter drive member (802) engages threading (836) of translation member (830). Because translation member (830) is rotatably and axially fixed within probe (701) through the securement of key feature (838) to probe (701), translation member (830) is responsive to counterclockwise rotation of cutter drive member (802) to provide proximal axial translation of cutter drive member (802) via engagement between threaded portion (822) and threading (836) of translation member (830).

Axial translation and rotation of cutter drive member (802) is then transferred to gate assembly (900) by the coupling between sample inspection member (902) and cutter drive member (802). Since cutter (730) is fixedly secured to sample inspection member (902), rotation and translation transferred to sample inspection member (902) is also transferred to cutter (730). Accordingly, as cutter drive member (802) is translated and rotated via drive gear (840)

and translation member (830), cutter (730) is correspondingly rotated and translated proximally, as seen in FIG. 27A.

Rotation and translation of cutter (730) via cutter drive member (802) continues until cutter (730) is positioned at a proximal position relative to lateral aperture (714). When cutter (730) is in the proximal position, cutter drive member (802) is correspondingly in a proximal position as shown in FIG. 26A. When cutter drive member (802) is in the proximal position, cutter drive member (802) is positioned within probe (701) such that translation member (830) and drive gear (840) are positioned distally relative to threaded portion (822) of cutter drive member (802). At this stage, holster (770) ceases rotation of drive gear (840), which correspondingly ceases rotation and translation of cutter drive member (802).

When cutter drive member (802) is in the proximal position, gate assembly (900) is in a corresponding open position. A transfer tube of cutter actuation assembly (800) generally remains stationary relative to cutter drive member (802) such that this configuration results in the transfer tube extending into the lumen of sample inspection member (902). In this instance, it should be understood that the transfer tube engages a gate slit (not shown) of gate assembly (900) to open the gate slit around the exterior of the transfer tube. Thus, when cutter drive member (802) is in the proximal position, gate assembly (900) is in an open position. In addition, when cutter drive member (802) is in the proximal position, cutter (730) is positioned in the proximal position such that lateral aperture (114) is in an open position, as seen in FIG. 27A. Accordingly, it should be understood that there is a relationship between gate assembly (900) and lateral aperture (814) such that when lateral aperture (814) is in the open position, gate assembly (900) is correspondingly in the open position. Likewise, when lateral aperture (714) is in the closed position, gate assembly (900) is in a corresponding closed position as shown in FIG. 27B.

Once lateral aperture (714) is in the open position, needle (710) is configured so that tissue may be prolapsed within lateral aperture (714). To prolapse tissue within lateral aperture (714), vacuum is applied to cutter (730) as similarly described above with respect to biopsy device (10). Once tissue is prolapsed into lateral aperture (714), a tissue sample can be severed via cutter (730) by driving cutter (730) distally. To drive cutter (730) distally, motor (790) rotates motor gear (780) counterclockwise as seen in FIG. 26B. In this instance, the meshed engagement of teeth (786) of motor gear (780) and teeth (848) of drive gear (840) causes drive gear (840) to rotate in a clockwise direction to initiate the same sequence described above but in an opposite direction. As cutter (730) is driven distally by cutter drive member (802), cutter drive member (802) and sample inspection member (902) both move distally until the tissue sample is severed by cutter (730), as seen in FIG. 27B.

With a tissue sample severed by distal translation of cutter (730), the severed tissue sample can next be transported proximally through cutter (730) and into sample inspection member (902). In particular, vacuum is applied to tissue sample holder (300), which flows into and through cutter drive member (802) and into the lumen (not shown) of sample inspection member (902). The vacuum flows from sample inspection member (902) into cutter (730) to transport the severed tissue sample through cutter (730) and into sample inspection member (902).

Once the severed tissue sample is transported into sample inspection member (902), the severed tissue sample is prevented from traveling further when gate assembly (900) is in the closed position. With the severed tissue sample positioned within sample inspection member (902), an operator can visually inspect the severed tissue sample with the naked eye due to the transparency of sample inspection member (902), which is visible through sample window (740) of probe (701). In some instances, gate assembly (900) may include a coupling collar (not shown) that is configured to selectively rotate sample inspection member (902) through a 360° view to thereby provide an operator with an increased opportunity to visually inspect the severed tissue sample.

Once an operator has completed visual inspection via sample window (740) and sample inspection member (902), the severed tissue sample can be transported to tissue sample holder (300). In particular, the severed tissue sample can be transported to tissue sample holder (300) by returning cutter (730), sample inspection member (902), and cutter drive member (802) to the proximal position shown in FIGS. 26A and 27A. As described above, this causes sample inspection member (902) and cutter drive member (802) to translate to position the transfer tube (not shown) of cutter actuation assembly (800) so that gate assembly (900) is in the open position. With gate assembly (900) in the open position, the severed tissue sample can be freely transported into the transfer tube, through gate assembly (900), and into tissue sample holder (300). At this stage, cutter (730) is also positioned in the proximal position so that lateral aperture (714) is in the open position. Accordingly, transporting the severed tissue sample to tissue sample holder (300) also prepares needle (710) for receipt of another tissue sample holder.

With the severed tissue sample received in tissue sample holder (300) an operator can next proceed by collecting one or more additional samples using the process described above with respect to the severed tissue sample. After collecting any suitable number of tissue samples, an operator may finalize the procedure by removing needle (710) from the patient, optionally marking the biopsy site, and sealing the opening in the patient. Any number of tissue samples collected during the biopsy procedure can finally be removed from tissue sample holder (300) and subjected to any desired tissue sample analysis procedure.

IV. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A biopsy device comprising: a body; a needle extending distally from the body; a cutter longitudinally translatable relative to the needle, wherein the cutter defines a cutter lumen; a tissue sample holder coupled proximally relative to the body, wherein the cutter lumen of the cutter defines at least a portion of a fluid conduit extending between the cutter and the tissue sample holder; and a sample stopping assembly, wherein the sample stopping assembly is configured to selectively arrest movement of a tissue sample within the fluid conduit between the cutter and the tissue sample holder.

Example 2

The biopsy device of Example 1, wherein the sample stopping assembly includes a sample inspection member and a gate seal.

Example 3

The biopsy device of Example 2, wherein at least a portion of the sample inspection member is transparent to permit visual inspection of a tissue sample through the sample inspection member.

Example 4

The biopsy device of Examples 2 or 3, wherein the sample inspection member and the gate seal are both movable relative to the body to transition the gate seal from a closed position to an open position.

Example 5

The biopsy device of any one or more of Examples 2 through 4, wherein the gate seal includes a plurality of vacuum openings, wherein the sample inspection member includes a plurality of vacuum channels, wherein the gate seal is positioned relative to the sample inspection member such that the vacuum openings of the gate seal are in fluid communication with the vacuum channels of the sample inspection member.

Example 6

The biopsy device of Example 5, wherein the vacuum channels of the sample inspection member together with the vacuum openings of the gate seal are configured to promote the flow of fluid through the gate seal when a tissue sample is adjacent to the gate seal.

Example 7

The biopsy device of any one or more of Examples 2 through 6, wherein the gate seal is flexible.

Example 8

The biopsy device of any one or more of Examples 2 through 7, further including a cutter actuation assembly, wherein the cutter actuation assembly is operable to drive movement of the cutter.

Example 9

The biopsy device of Example 8, wherein the cutter actuation assembly includes a cutter drive member, wherein at least a portion of the cutter drive member is configured to secure the gate seal to the sample inspection member of the gate assembly.

Example 10

The biopsy device of Example 9, wherein the sample inspection member includes a lumen, wherein the cutter drive member includes a lumen, wherein the lumens of the sample inspection member and the cutter drive member both define a portion of the fluid conduit extending between the cutter and the tissue sample holder.

Example 11

The biopsy device of any one or more of Examples 2 through 10, wherein the gate seal is configured to transition between an open configuration and closed configuration, wherein the gate seal includes a plurality of openings, wherein each opening of the plurality of openings is configured to permit communication of fluid through the gate seal when the gate seal is in both the open configuration and the closed configuration.

Example 12

The biopsy device of any one or more of Examples 1 through 11, wherein the sample stopping assembly includes a sample inspection member, the sample inspection member including a sensor to detect the presence of a tissue sample within the sample inspection member.

Example 13

The biopsy device of Example 12, wherein the sensor is in communication with a controller, wherein the controller is configured to reduce vacuum supplied to the tissue sample holder in response to detection of the presence of a tissue sample by the sensor.

Example 14

The biopsy device of Example 13, wherein the sensor includes an impedance sensor, wherein the controller is configured to identify characteristics of a tissue sample based on signals from the impedance sensor.

Example 15

The biopsy device of Example 12, wherein the sample inspection member includes access window, wherein the access window is configured to move between an open configuration and a closed configuration to permit removal of a tissue sample from the sample inspection member.

Example 16

A biopsy device comprising: a body; a needle extending distally from the body; a cutter longitudinally translatable relative to the needle, wherein the cutter defines a cutter lumen; a tissue sample holder coupled proximally relative to the body, wherein the cutter lumen of the cutter defines at least a portion of a fluid conduit extending between the cutter and the tissue sample holder; and a cutter actuation assembly, wherein the cutter actuation assembly includes a cutter driver in communication with the cutter, a translation member, and a drive gear, wherein the cutter driver includes a threaded portion having a plurality of threads, wherein the threads are interrupted by a channel extending laterally along the threaded portion, wherein the translation member is configured to engage the threaded portion to translate the cutter via the cutter driver, wherein the drive gear is configured to engage the channel to rotate the cutter via cutter driver.

Example 17

The biopsy device of Example 16, wherein the translation member includes a body defining a bore, wherein the body further defines threading extending inwardly within the bore, wherein the threading is configured to mesh with the threads of the cutter driver.

Example 18

The biopsy device of Example 17, wherein the threading defined by the body of the translation member includes a single thread defined by a single turn around the interior of the bore.

Example 19

The biopsy device of Example 17, wherein the threading defined by the body of the translation member includes a plurality of threads.

Example 20

The biopsy device of any one or more of Examples 16 through 19, wherein the translation member includes at least one key configured to engage at least a portion of the body such that the translation member is secured in a fixed position relative to the body.

Example 21

The biopsy device of any one or more of Examples 16 through 20, wherein the cutter driver is configured to actuate a tissue stopping assembly, wherein the tissue stopping assembly includes a seal, wherein the cutter driver is configured to move the seal while simultaneously moving the cutter.

Example 22

The biopsy device of Example 21, wherein the cutter driver is configured to move the seal relative to a transfer tube to transition the seal between an open and closed position.

Example 23

The biopsy device of Example 22, wherein the cutter driver defines a lumen, wherein the lumen of the cutter driver is configured to receive the transfer tube such that the transfer tube is slidable within the lumen of the cutter driver.

Example 24

The biopsy device of any one or more of Examples 16 through 23, wherein the drive gear defines a bore configured to receive the cutter driver, wherein the drive gear includes at least one protrusion, wherein the protrusion is configured to engage the channel of the cutter driver to transfer rotation of the drive gear to the cutter driver.

Example 25

The biopsy device of Example 24, wherein the cutter driver defines two channels, wherein the drive gear includes two protrusions corresponding to each channel of the drive gear.

Example 26

A biopsy device comprising: a holster; a probe including a needle extending distally from the probe and a cutter longitudinally translatable relative to a lateral aperture defined by the needle, wherein the cutter defines a cutter lumen; a tissue sample holder associated with the probe; a transfer tube at least partially defining a conduit extending between the cutter and the tissue sample holder; and a sample stopping assembly, wherein the sample stopping assembly includes a seal configured to arrest proximal movement of a tissue sample disposed within the conduit, wherein the seal is movable relative to the transfer tube to transition between an open configuration and a closed configuration.

Example 27

The biopsy device of Example 26, wherein the sample stopping assembly includes a sample inspection member, the sample inspection member including a sensor to detect the presence of a tissue sample within the sample inspection member.

Example 28

The biopsy device of Example 27, wherein the sensor is in communication with a controller, wherein the controller is configured to reduce vacuum supplied to the tissue sample holder in response to detection of the presence of a tissue sample by the sensor.

Example 29

The biopsy device of Example 28, wherein the sensor includes an impedance sensor, wherein the controller is configured to identify characteristics of a tissue sample based on signals from the impedance sensor.

Example 30

The biopsy device of any one or more of Examples 27 through 29, wherein the sample inspection member includes access window, wherein the access window is configured to move between an open configuration and a closed configuration to permit removal of a tissue sample from the sample inspection member.

Example 31

The biopsy device of any one or more of Examples 26 through 30, wherein the seal of the sample stopping assembly includes a plurality of openings, wherein the openings are configured to communicate fluid through the seal when the seal is in both the open configuration and the closed configuration.

Example 32

The biopsy device of Example 31, wherein the seal of the sample stopping assembly further includes a slot, wherein the transfer tube is configured to penetrate the slot to transition the seal to the open configuration.

Example 33

The biopsy device of Example 32, wherein the transfer tube is configured to penetrate the slot of the seal upon movement of the seal relative to the transfer tube.

Example 34

The biopsy device any one or more of Examples 26 through 33, wherein the cutter is configured to translate between a proximal position and a distal position, wherein the seal is configured to translate with the cutter as the cutter translates between the proximal position and the distal position.

Example 35

The biopsy device of Example 34, wherein the seal is configured to be in the open configuration when the cutter is in the proximal position, wherein the seal is configured to be in the closed configuration when the cutter is on the distal position.

Example 36

A method for collecting tissue samples using a biopsy device, the method comprising: transporting a first tissue sample through a cutter of the biopsy device to a sample viewing portion of the biopsy device; arresting the first tissue sample in the sample viewing portion; inspecting the first tissue sample while the first tissue sample is disposed within the viewing portion; transporting the first tissue sample from the sample viewing portion to a tissue sample holder; and transporting a second tissue sample through the cutter to the sample viewing portion.

Example 37

The method of Example 36, wherein the step of inspecting the first tissue sample includes visual inspection of the first tissue sample.

Example 38

The method of any one or more of Examples 36 through 37, further comprising removing the first tissue sample from the sample viewing portion to inspect the first tissue sample by palpitation.

Example 39

The method of any one or more of Examples 36 through 38, further comprising retracting the cutter proximally relative to a needle of the biopsy device to open a seal positioned adjacent to the sample viewing portion.

Example 40

The method of Example 39, further comprising advancing the cutter distally relative to the needle to close the seal.

Example 41

A biopsy device comprising: a body; a needle extending distally from the body; a cutter longitudinally translatable relative to the needle, wherein the cutter defines a cutter lumen; a tissue sample holder coupled to the body, wherein the cutter lumen of the cutter defines at least a portion of a fluid conduit extending between the cutter and the tissue sample holder; and a sample stopping assembly disposed between a distal end of the cutter and the tissue sample holder, wherein the sample stopping assembly is configured to selectively stop a tissue sample being transported within the fluid conduit for inspection and to allow the movement of the stopped tissue sample towards the tissue sample holder.

Example 42

The biopsy device of Example 41, wherein the sample stopping assembly includes a transparent sample inspection window to permit visual inspection of the stopped tissue sample.

Example 43

The biopsy device of Example 42, wherein the sample inspection window and the gate seal are both movable relative to the body to transition the gate seal from a closed position that stops the tissue sample to an open position that allows movement of the stopped tissue sample towards the tissue sample holder.

Example 44

The biopsy device of Example 42, wherein the gate seal includes a plurality of vacuum openings, wherein the sample inspection window includes a plurality of vacuum channels, wherein the gate seal is positioned relative to the sample inspection window such that the vacuum openings of the gate seal are in fluid communication with the vacuum channels of the sample inspection window.

Example 45

The biopsy device of Example 44, wherein the vacuum channels of the sample inspection window together with the vacuum openings of the gate seal are configured to promote the flow of fluid through the gate seal when a tissue sample is adjacent to the gate seal.

Example 46

The biopsy device of any one or more of Examples 42 through 45, wherein the gate seal is flexible.

Example 47

The biopsy device of any one or more of Examples 42 through 46, further including a cutter actuation assembly, wherein the cutter actuation assembly is operable to drive movement of the cutter.

Example 48

The biopsy device of Example 47, wherein the cutter actuation assembly includes a cutter drive member, wherein at least a portion of the cutter drive member is configured to secure the gate seal to the sample inspection window of the gate assembly.

Example 49

The biopsy device of Example 48, wherein the sample inspection window includes a lumen, wherein the cutter drive member includes a lumen, wherein the lumens of the sample inspection member and the cutter drive member both define a portion of the fluid conduit extending between the cutter and the tissue sample holder.

Example 50

The biopsy device of any one or more of Examples 42 through 49, wherein the gate seal is configured to transition between an open configuration and closed configuration, wherein the gate seal includes a plurality of openings, wherein each opening of the plurality of openings is configured to permit communication of fluid through the gate seal when the gate seal is in both the open configuration and the closed configuration.

Example 51

The biopsy device of any one or more of Examples 42 through 50, wherein the biopsy device further includes a transport tube extending distally from the tissue sample holder, wherein the transport tube defines at least a portion of the fluid conduit, wherein the transport tube is configured to transition the gate seal from a closed position that stops the tissue sample to an open position that allows movement of the stopped tissue sample towards the tissue sample holder upon movement of the gate seal relative to the transport tube.

Example 52

The biopsy device of Example 41, wherein the sample stopping assembly is associated with a sensor, wherein the sensor is configured to detect the presence of the stopped tissue sample within at least a portion of the sample stopping assembly.

Example 53

The biopsy device of Example 52, wherein the sensor is in communication with a controller, wherein the controller is configured to reduce vacuum supplied to the tissue sample holder in response to detection of the presence of a tissue sample by the sensor.

Example 54

The biopsy device of any one or more of Examples 52 through 53, wherein the sensor is integrated into at least a portion of the sample stopping assembly.

Example 55

The biopsy device of any one or more of Examples 52 through 53, wherein the sensor is integrated into the body.

V. CONCLUSION

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Embodiments of the devices disclosed herein can be reconditioned for reuse after at least one use. Reconditioning may include any combination of the steps of disassembly of the device, followed by cleaning or replacement of particular pieces, and subsequent reassembly. In particular, embodiments of the devices disclosed herein may be disassembled, and any number of the particular pieces or parts of the devices may be selectively replaced or removed in any combination. Upon cleaning and/or replacement of particular parts, embodiments of the devices may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. A biopsy device comprising:
    (a) a body;
    (b) a needle extending distally from the body;
    (c) a cutter tube longitudinally translatable and rotatable relative to the needle;
    (d) a tissue sample holder coupled to the body;
    (e) a sample stopping assembly disposed between a distal end of the cutter tube and the tissue sample holder, the sample stopping assembly being configured to stop a tissue sample being transported through the body from the cutter tube to the tissue sample holder; and (f) an inspection window attached to a portion of the sample stopping assembly and the cutter tube, the inspection window being configured to rotate and translate the cutter tube simultaneously relative to the body via rotation and translation communicated to the inspection window by the portion of the sample stopping assembly.

2. The biopsy device of claim 1, the inspection window being configured to permit visual inspection of the tissue sample stopped by the sample stopping assembly.

3. The biopsy device of claim 1, the portion of the sample stopping assembly including a gate having a gate seal, the inspection window and the gate seal being both operable to move relative to the body to transition the gate seal from a closed position that stops the tissue sample to an open position that allows communication of the tissue sample towards the tissue sample holder.

4. The biopsy device of claim 1, the portion of the sample stopping assembly including a gate having a gate seal, the gate seal including a plurality of vacuum openings, the inspection window defining a plurality of vacuum channels, the gate seal being positioned relative to the inspection window such that the vacuum openings of the gate seal are in fluid communication with the vacuum channels of the inspection window.

5. The biopsy device of claim 4, the vacuum channels of the inspection window together with the vacuum openings of the gate seal being configured to promote a flow of fluid through the gate seal when the tissue sample is adjacent to the gate seal.

6. The biopsy device of claim 4, the gate seal being flexible.

7. The biopsy device of claim 1, further comprising a cutter actuation assembly operable to drive movement of the cutter tube, the cutter actuation assembly including a cutter drive member, the portion of the sample stopping assembly including a gate having a gate seal, at least a portion of the cutter drive member being configured to secure the gate seal to the inspection window.

8. The biopsy device of claim 7, the inspection window including a lumen, the cutter drive member including a lumen, the lumens of the inspection window and the cutter drive member both defining a portion of a fluid conduit extending between the cutter tube and the tissue sample holder.

9. The biopsy device of claim 1, the portion of the sample stopping assembly including a gate having a gate seal, the gate seal being configured to transition between an open configuration and a closed configuration, the gate seal including a plurality of openings, each opening of the plurality of openings being configured to permit communication of fluid through the gate seal when the gate seal is in both the open configuration and the closed configuration.

10. The biopsy device of claim 1, further comprising a transport tube extending distally from the tissue sample holder, the portion of the sample stopping assembly including a gate having a gate seal, the transport tube being configured to transition the gate seal from a closed position that stops the tissue sample to an open position that allows communication of the tissue sample towards the tissue sample holder via the transport tube.

11. The biopsy device of claim 1, further comprising a controller and a vacuum source in communication with the controller configured to apply a vacuum to the tissue sample holder, the inspection window including a sensor to detect a presence of the tissue sample within the inspection window, the sensor being in communication with the controller, the controller being configured to reduce the vacuum applied to the tissue sample holder by the vacuum source in response to the detection of the presence of the tissue sample by the sensor.

12. The biopsy device of claim 1, further comprising a controller, the inspection window including a sensor to detect a presence of the tissue sample within the inspection window, the sensor including an impedance sensor, the controller being configured to identify characteristics of the tissue sample based on signals from the impedance sensor.

13. The biopsy device of claim 1, the inspection window including an access point, the access point being configured to move between an open configuration and a closed configuration to permit removal of the tissue sample from the inspection window.

14. The biopsy device of claim 1, the portion of the sample stopping assembly including a gate having a gate seal, the gate seal being configured to move relative to the body to transition the gate seal to a closed position in response to distal translation of the cutter tube, the gate seal being further configured to move relative to the body to transition to an open position in response to proximal translation of the cutter tube.

15. The biopsy device of claim 1, the portion of the sample stopping assembly including a gate having a gate seal, the gate seal including a sample opening and being configured to move relative to the body to transition the sample opening between a closed position and an open position.

16. A biopsy device comprising:
(a) a body;
(b) a needle extending distally from the body;
(c) a cutter longitudinally translatable and rotatable relative to the needle, the cutter defining a cutter lumen;
(d) a tissue sample holder coupled to the body;
(e) a transparent inspection member operatively coupled to the cutter to transmit rotation and translation of the transparent inspection member to the cutter; and
(f) a sample stopping assembly operable to selectively stop movement of a tissue sample within the inspection member before being transported to the tissue sample holder from the cutter, the sample stopping assembly being configured to transmit rotation and translation to the transparent inspection member to rotate the cutter via the transparent inspection member.

17. The biopsy device of claim 16, further comprising a transport tube extending distally from the tissue sample holder, the transport tube being in fluid communication with the tissue sample holder and the inspection member.

18. The biopsy device of claim 17,
further comprising a gate seal, the gate seal being elastomeric;
the transport tube being immovably fixed to the body; and
the sample stopping assembly being configured such that proximal movement of the sample stopping assembly towards the transport tube allows a distal end of the transport tube to penetrate and enlarge an elastomeric opening defined by the gate seal.

19. The biopsy device of claim 16, further comprising a transport tube extending distally from the tissue sample holder, the transport tube being in fluid communication with the tissue sample holder, the sample stopping assembly including a gate having a gate seal, the gate seal including a sample slit and being configured to move relative to the transport tube to transition the sample slit between a closed position and an open position.

20. A biopsy device comprising:
  (a) a body;
  (b) a needle extending distally from the body;
  (c) a cutter longitudinally translatable and rotatable relative to the needle, the cutter defining a cutter lumen and an open proximal end;
  (d) a tissue sample holder coupled to the body;
  (e) an inspection member extending proximally from the proximal end of the cutter and having an inspection lumen aligned coaxially with the cutter lumen; and
  (f) a sample stopping assembly operable to selectively stop movement of a tissue sample being transported to the tissue sample holder from the cutter, the sample stopping assembly, the inspection member, and the cutter being configured to rotate together relative to the body.

* * * * *